(12) United States Patent
Jongerius

(10) Patent No.: US 12,115,566 B2
(45) Date of Patent: Oct. 15, 2024

(54) SYSTEM FOR PLANAR UV-C BASED BIOFOULING PREVENTION

(71) Applicant: KONINKLIJKE PHILIPS N.V., Eindhoven (NL)

(72) Inventor: Michel Johannes Jongerius, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1018 days.

(21) Appl. No.: 17/040,562

(22) PCT Filed: Mar. 22, 2019

(86) PCT No.: PCT/EP2019/056623
§ 371 (c)(1),
(2) Date: Sep. 23, 2020

(87) PCT Pub. No.: WO2019/197113
PCT Pub. Date: Oct. 17, 2019

(65) Prior Publication Data
US 2021/0046521 A1 Feb. 18, 2021

(30) Foreign Application Priority Data
Mar. 27, 2018 (EP) .................................... 18164192

(51) Int. Cl.
*B08B 7/00* (2006.01)
*A61L 2/10* (2006.01)
(Continued)

(52) U.S. Cl.
CPC .............. *B08B 7/0057* (2013.01); *A61L 2/10* (2013.01); *A61L 2/24* (2013.01); *B08B 17/00* (2013.01);
(Continued)

(58) Field of Classification Search
CPC .......... A61L 2/10; A61L 2/24; A61L 2202/11; G02B 6/0003; G02B 6/0066; F21V 9/30; B08B 7/0057; B08B 17/00
See application file for complete search history.

(56) References Cited

U.S. PATENT DOCUMENTS

| 8,421,037 B2 | 4/2013 | Leard |
| 9,611,016 B2 | 4/2017 | Salters et al. |

(Continued)

FOREIGN PATENT DOCUMENTS

| WO | 2014188347 A1 | 11/2014 |
| WO | 2016192942 A1 | 12/2016 |

(Continued)

OTHER PUBLICATIONS

Bart Salters and Richard Piola, UVC Light for Antifouling, Marine Technology Society Journal, 51, No. 2, 59-70, 2017.
(Continued)

*Primary Examiner* — Sean E Conley

(57) ABSTRACT

A system (200) comprising a light source (220) configured to generate light source radiation (221), wherein the light source radiation (221) at least comprises UV radiation, wherein the system (200) further comprises a luminescent material (400) configured to convert part of the light source radiation (221) into luminescent material radiation (401), wherein the luminescent material radiation (401) comprises one or more of visible light and infrared radiation, wherein the system (200) is configured to generate system light (201) comprising the light source radiation (221) and the luminescent material radiation (401).

20 Claims, 9 Drawing Sheets

(51) Int. Cl.
  *A61L 2/24*    (2006.01)
  *B08B 17/00*   (2006.01)
  *B63B 59/04*   (2006.01)
  *F21V 8/00*    (2006.01)
  *F21V 9/30*    (2018.01)

(52) U.S. Cl.
  CPC ............... *B63B 59/04* (2013.01); *F21V 9/30* (2018.02); *G02B 6/0003* (2013.01); *G02B 6/0066* (2013.01); *A61L 2202/11* (2013.01)

(56) References Cited

U.S. PATENT DOCUMENTS

| | | |
|---|---|---|
| 2009/0067194 A1 | 3/2009 | Sanchez |
| 2009/0141476 A1 | 6/2009 | Meir |
| 2017/0122529 A1 | 5/2017 | Yamada |
| 2018/0099317 A1 | 4/2018 | Salters et al. |

FOREIGN PATENT DOCUMENTS

| | | |
|---|---|---|
| WO | 2016193114 A1 | 12/2016 |
| WO | 2017009394 A | 1/2017 |

OTHER PUBLICATIONS

International Search Report and Written Opinion from PCT/EP2019/056623 mailed Sep. 2, 2019.

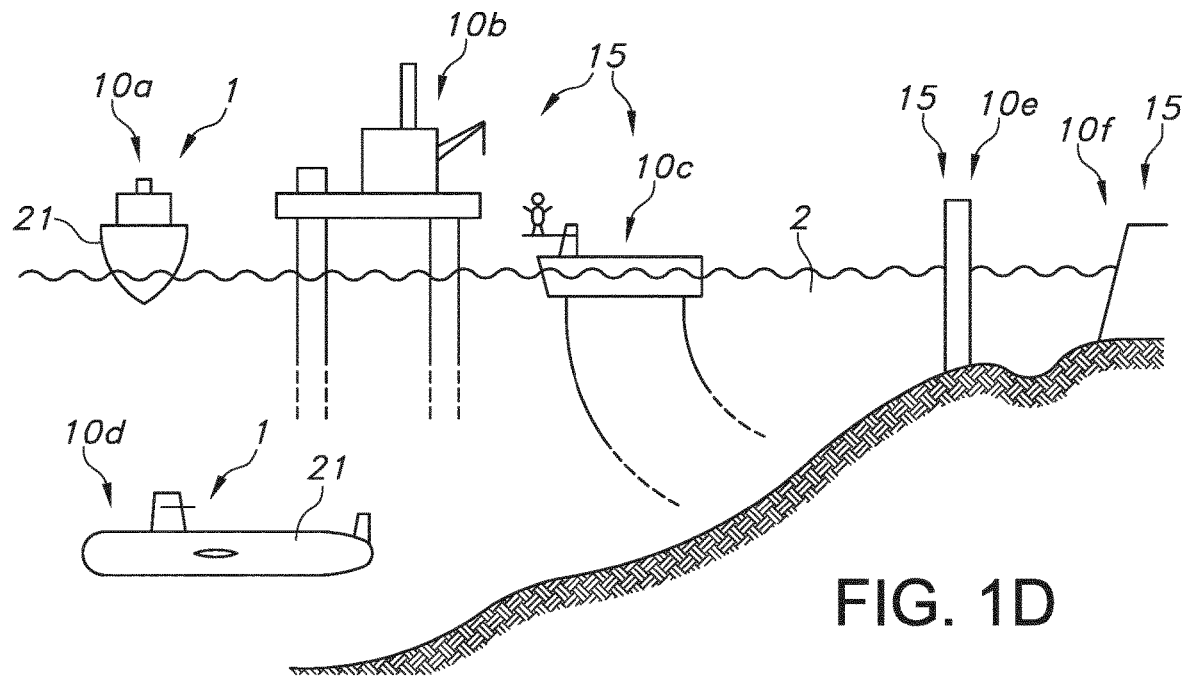
FIG. 1D
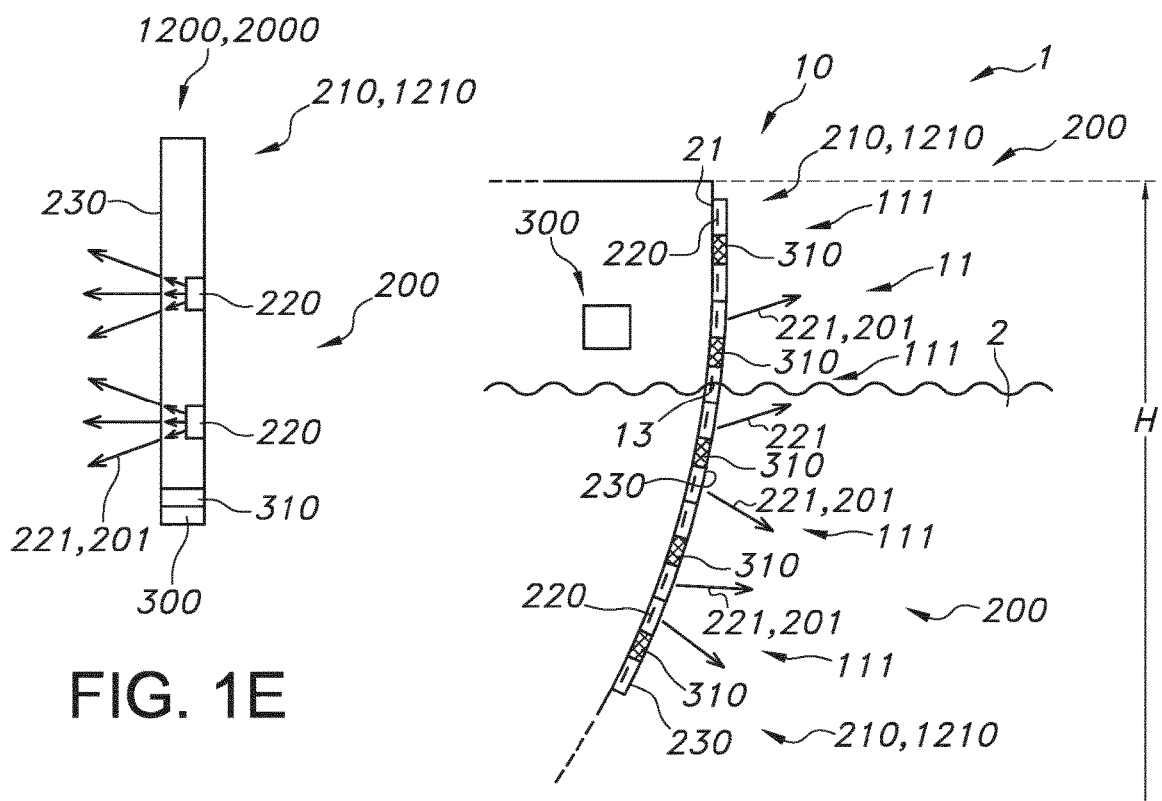
FIG. 1E
FIG. 1F

SYSTEM FOR PLANAR UV-C BASED BIOFOULING PREVENTION

CROSS REFERENCE TO RELATED APPLICATIONS

This application is a U.S. national phase application of International Application No. PCT/EP2019/056623 filed on Mar. 22, 2019, which claims the benefit of EP Application Serial No. 18164192.9 filed on Mar. 27, 2018 and are incorporated herein by reference.

FIELD OF THE INVENTION

The invention relates to an (anti-biofouling) system. The invention also relates to an object which includes such (anti-biofouling) system. Further, the invention relates to a method for providing such waveguide or (anti-biofouling) system to an object. The invention also relates to a computer program product for controlling such (anti-biofouling) system.

BACKGROUND OF THE INVENTION

Anti-biofouling methods are known in the art. WO 2016192942 A1 (Koninklijke Philips N.V.), for instance, describes an object that during use is at least partly submerged in water, the object further comprising an anti-biofouling system comprising an UV emitting element for application of UV radiation, wherein the UV emitting element especially comprises one or more light sources, even more especially one or more solid state light sources, and is configured to irradiate with said UV radiation (during an irradiation stage) one or more of (i) a (said) part of said external surface and (ii) water adjacent to said part of said external surface, wherein the object is especially selected from the group consisting of a vessel and an infrastructural object.

WO 2016193114 describes an object that during use is at least partly submerged in water, the object further comprising an anti-biofouling system comprising an UV emitting element for application of UV radiation (to a part of an external surface of the object), wherein the UV emitting element especially comprises one or more light sources, even more especially one or more solid state light sources, and is configured to irradiate with said UV radiation (during an irradiation stage) one or more of (i) a (said) part of said external surface and (ii) water adjacent to said part of said external surface, wherein the object is especially selected from the group consisting of a vessel and an infrastructural object. The UV emitting element may especially comprise a UV radiation escape surface. Hence, in a specific embodiment the UV emitting element comprises a UV radiation escape surface, with the UV emitting element especially being configured to provide said UV radiation downstream from said UV radiation escape surface of said UV emitting element. Such UV radiation escape surface may be an optical window through which the radiation escapes from the UV emitting element. Alternatively or additionally, the UV radiation escape surface may be the surface of a waveguide. Hence, UV radiation may be coupled in the UV emitting element into the waveguide, and escape from the element via a (part of a) face of the waveguide. In a specific embodiment, the UV emitting element comprises a luminescent material configured to absorb part of the UV radiation and convert into visible luminescent material light (i.e. visible light generated by the luminescent material upon excitation with the UV radiation), wherein the light source and said luminescent material are configured to provide said visible luminescent material light emanating in a direction away from the external surface. Optionally, the anti-biofouling system is configured to provide said luminescent material light in a pulsed way. Hence, in this way, a person at a distance from the object (and thus external from the object) may perceive the luminescence, e.g. a red blinking light.

US20090141476 describes an illumination apparatus comprising: a waveguide having a first surface; embedded within the waveguide, (i) a light-emitting source for emitting source light, and (ii) a photoluminescent material for converting some of the source light to a different wavelength, the converted source light mixing with unconverted source light to form output light spectrally different from both the converted source light and the unconverted source light, wherein output light is emitted from at least a portion of the first surface. Amongst others, US20090141476 describes a source light which may include at least one of blue light or ultraviolet light, or substantially white light. For instance, an apparatus comprises one or more light-emitting sources embedded in a waveguide material having a first surface and a second surface. Waveguide material is capable of propagating light generated by each light source such that at least a portion of the light is diffused within waveguide material and exits through at least a portion of first surface. The output light comprises substantially white light.

SUMMARY OF THE INVENTION

Biofouling or biological fouling (herein also indicated as "fouling" or "biofouling") is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community. Herein, "biofouling" may in embodiments also related to bacteria.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Non-toxic mechanical strategies that prevent organisms from attaching include choosing a material or coating with a slippery surface, or creation of nanoscale surface topologies similar to the skin of sharks and dolphins which only offer poor anchor points. Biofouling on the hull of ships causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

It surprisingly appears that one may effectively use UV radiation to substantially prevent biofouling on surfaces that are in contact with sea water or water in lakes, rivers, canals, etc. Herewith, an approach is presented based on optical methods, in particular using ultra-violet light or radiation (UV). It appears that most micro-organisms are killed, rendered inactive or unable to reproduce with sufficient UV light. This effect is mainly governed by the total dose of UV light. A typical dose to kill 90% of a certain micro-organism is 10 mW/h/m$^2$.

In specific embodiments, an average dose (of the UV radiation) over time is selected from the range of at least 10 J/m$^2$, like especially selected from the range of 100-3000 J/m$^2$.

Especially good results may be obtained with a substantial constant UV radiation of at least about $0.5*10^{-9}$ Watt/mm$^2$, like at least about $10^{-9}$ Watt/mm$^2$, such as at least about $1.5*10^{-9}$ Watt/mm$^2$, relative to the area of the light emissive surface, like no more than $10^{-6}$ Watt/mm$^2$, such as no more than $0.5*10^{-7}$ Watt/mm$^2$, like no more than $10^{-7}$ Watt/mm$^2$.

UV LEDs or UV sources may operate with limited wall plug efficiency and limited lifetime. This may limit the use of such light sources.

UV radiation, however, can also be used for applications other than anti-fouling of aquatic (such as marine) objects. UV radiation may also be used to clean objects or to keep objects clean from bacteria, etc.

The term "aquatic" and similar terms may refer to both freshwater and salt water applications (and of course also brackish water applications).

In all such examples, it may be necessary to take specific measures when higher organisms, including humans, may receive such UV radiation, especially when it is possible to physically contact radiation emitting surfaces.

Light sources are used for providing the anti-biofouling light. For optimal operation of the light source or system, it may be that the intensity of the light provided is (locally) more than necessary. For instance, when using a waveguide, in order for rays to generate large enough intensities to ensure antifouling (over the whole waveguide surface) the light sources, such as LEDs, have to produce considerable amounts of UVC light, causing the intensity of rays near the light sources such as LEDs, to be at intensity above the required anti-fouling threshold. This may lead to an ineffective use of the overall UVC power generated.

Hence, it is an aspect of the invention to provide an alternative system or method for prevention or reduction of biofouling, which preferably further at least partly obviates one or more of above-described drawbacks. The present invention may have as object to overcome or ameliorate at least one of the disadvantages of the prior art, or to provide a useful alternative.

In a first aspect, the invention provides a system comprising a light source configured to generate light source radiation, wherein the light source radiation at least comprises UV radiation, wherein the system further comprises a luminescent material also be indicated as "phosphor") configured to convert part of the light source radiation into luminescent material radiation, wherein the luminescent material radiation comprises visible light (and/or IR radiation), wherein the system is configured to generate system light comprising the light source radiation (especially the UV radiation) and the luminescent material radiation. The terms "radiation" and "light" may interchangeably be used.

In a further aspect, the invention provides a system comprising (i) a light source configured to generate light source radiation, wherein the light source radiation at least comprises UV radiation (such as UV-C radiation), (ii) a luminescent material configured to convert part of the light source radiation (especially at least part of the UV radiation) into luminescent material radiation, wherein the luminescent material radiation comprises one or more of (a) visible light and (b) infrared radiation, and optionally (iii) an attenuation element configured downstream of the light source and upstream of the luminescent material, wherein the attenuation element is configured to transmit part of the light source radiation (especially part of the UV radiation) (and especially also to reflect at least part of the luminescent material radiation), wherein the system is configured to generate system light comprising the light source radiation (especially at least including UV radiation) and the luminescent material radiation.

In yet a further aspect, the invention provides a system comprising (i) a light source configured to generate light source radiation, wherein the light source radiation at least comprises UV radiation (such as UV-C radiation), (ii) a luminescent material configured to convert part of the light source radiation (especially at least part of the UV radiation) into luminescent material radiation, wherein the luminescent material radiation comprises one or more of (a) visible light and (b) infrared radiation, and optionally (iii) a semi-transparent mirror configured downstream of the light source and upstream of the luminescent material, wherein the semi-transparent mirror is configured to transmit part of the light source radiation (especially part of the UV radiation) (and especially also to reflect at least part of the luminescent material radiation), wherein the system is configured to generate system light comprising the light source radiation (especially at least including UV radiation) and the luminescent material radiation.

Hence, by using a luminescent material superfluous UV radiation may be absorbed and at least partly converted into (useful) visible light and/or other type of radiation. In this way, useful visible light (and/or other type of radiation) and useful UV radiation is generated. The optical properties of the visible light may be chosen in line with a dedicated purpose, such as the color of material surrounding the light source, or a unit comprising the light source. It may also be possible to make the spectral properties of luminescent material radiation controllable when different luminescent materials are applied and when a plurality of light sources may be applied. Further, it may also be possible to control an inhomogeneous light distribution of planar light output device, such as e.g. a light output device using a waveguide for distributing the UV light over the waveguide.

As indicated above, the invention provides a system comprising a light source configured to generate light source radiation, wherein the light source radiation at least comprises UV radiation. The UV radiation may especially be used for anti-biofouling purposes. As the system may be used to neutralize bacteria and/or other microorganisms, or to prevent attachment of bacteria and/or microorganisms, the anti-biofouling system may in general also be indicated as "system" and in specific embodiments "anti-micro biological fouling system", or "hygiene system", etcetera. Herein, the system may further be indicated as "anti-biofouling system" or "system".

Especially, the system comprises a UV-emitting element. In embodiments, such UV emitting element may comprise a light source with a plurality of light emitting surfaces. In embodiments, such UV emitting element may comprise a plurality of light sources, such as configured in an array, such as e.g. to provide a relative broad beam of UV radiation. For instance, the UV emitting element may comprise a light emitting diode device comprising a plurality of nanowires or nano pyramids grown on a graphitic substrate, said nanowires or nano pyramids having a p-n or p-i-n junction, a first electrode in electrical contact with said graphitic substrate, a second electrode in contact with the top of at least a portion of said nanowires or nano pyramids optionally in the form of a light reflective layer, wherein said nanowires or nano pyramids comprise at least one group III-V compound semiconductor, such as e.g. described in WO2017009394A. Such UV emitting element may also comprise a waveguide, such as for distributing UV radiation over at least part of a surface of the waveguide. In all embodiments, the UV emitting element is configured to generate UV radiation during operation, though other radiation accompanying this UV radiation is not excluded herein. Some of these embodiments are described in more detail below.

As indicated above, the system further comprises a luminescent material configured to convert part of the light source radiation into luminescent material radiation. Hence, not all UV radiation generated (during operation of the system) is absorbed and at least partly converted by the luminescent material. Nevertheless, the invention is also directed to embodiments wherein locally the luminescent material may absorb all UV radiation that is locally directed to the luminescent material. For instance, as also indicated below in more detail the luminescent material may be configured in a pattern, wherein there may be regions with total absorption of the UV radiation (and conversion into luminescent material radiation) and regions with less or no absorption of the UV radiation (and relatively less or no conversion into luminescent material radiation). The luminescent material may be considered radiationally coupled with the light source. The term "radiationally coupled" especially means that the light source and the luminescent material are associated with each other so that at least part of the radiation emitted by the light source is received by the luminescent material (and at least partly converted into luminescence).

In embodiments, the system may comprise a plurality of light sources. Especially, in embodiments for each light source of the plurality of light sources may apply that part of its light source light may be converted into luminescent material light, and part of its unconverted light source light becomes, like the luminescent material light, part of the system light. Hence, in embodiments part of the UV radiation of the light source is converted into luminescent material light, and part of the UV radiation of the light source is not converted. Therefore, in embodiments the system light comprises the UV radiation of each of the light sources of the plurality of light sources, as well as luminescent material light that is generated by part of the UV radiation of each of the light sources of the plurality of light sources.

Hence, the invention also provides an embodiment of the system, wherein the system comprises a plurality of the light sources, wherein each light source is configured to generate light source radiation, wherein the light source radiation at least comprises UV radiation, wherein the system further comprises (ii) the luminescent material configured to convert part of the light source radiation of each of the light sources into the luminescent material radiation, wherein system light comprises the light source radiation of each of the light sources and the luminescent material radiation.

As indicated above, a semi-transparent mirror may be applied, amongst others to attenuate the luminescent material light and/or redistribute the light source light. Such semi-transparent mirror may be optically coupled to each of the light sources of the plurality of light sources.

Hence, the invention also provides in specific embodiments such system further comprising a plurality of the semi-transparent mirrors, configured downstream of each of the light sources and upstream of the luminescent material. In yet further specific embodiments, each of the light sources and each of the semi-transparent mirrors are configured to provide at least part of the UV radiation of the respective light source in a direction perpendicular to the respective semi-transparent mirror and at least part of the UV radiation of the respective light source in a direction parallel to the respective semi-transparent mirror.

In embodiments, the luminescent material may be provided as layer on a surface downstream of the light sources. Such luminescent material layer is thus especially configured such that part of the light source light is transmitted through the layer. The luminescent material may be provided as patterned layer, comprising a plurality of areas with luminescent material, wherein in embodiments each area of luminescent material is configured downstream of a respective light source. The plurality of areas of luminescent materials are alternated in the pattern with areas with no luminescent material, or areas with a thin layer of luminescent material, or another type of areas that have a higher transmission for the light source light than the areas with luminescent material. Combinations of different types of areas may also be applied.

In specific embodiments, the plurality of light sources may be provided by a two-dimensional grid of light sources for generating UV radiation. For instance, in embodiments such grid of light source may be aligned with a pattern of luminescent material. In other embodiments, such grid of light sources may comprise a subset of first light sources of which the light source light is comprised by the system light, and another subset of light sources, of which the light source light is partly converted by the luminescent material, and partly the light source light is also comprised by the system light. In yet embodiments, each of the light sources comprised by the grid may be optically coupled with a respective semi-transparent mirror.

The phrases "configured to convert part of the light source radiation into luminescent material radiation" and "wherein the system is configured to generate system light comprising the light source radiation and the luminescent material radiation", and similar phrases, especially indicate that part of the UV radiation of the light source is converted into luminescent material light, and part of the UV radiation is not converted by the luminescent material light, leading to lighting system light comprising (1) luminescent material light of the luminescent material, based upon conversion of UV radiation of the light source, and (2) non-converted UV radiation of the (same) light source.

In specific embodiments, all light sources 220 comprise solid state light sources.

In embodiments, the amount of UV radiation absorbed and at least partly converted by the luminescent material may be equal to or larger than 2%, such as equal to or larger than 5%, such as equal to or larger than 10% of the total power (Watt) of the UV radiation, but equal to or smaller than 98%, such as equal to or smaller than 95%, such as equal to or smaller than 90%, like equal to or smaller than 80%, such as especially equal to or smaller than 60% of the total power of the UV radiation provided by the light source(s). Hence, at least 2%, such as at least 5%, such as at least 10%, like at least 20%, such as at least 40% of the UV radiation generated by the light sources is not converted by the luminescent material. Hence, the system light has a total power, of which at least 2%, such as at least 5%, such as at least 10%, like at least 20%, such as at least 40% of the total power is UV radiation, and at least 2%, such as at least 5%, such as at least 10% may be absorbed and at least partly converted into luminescent material radiation (with the latter being selected from the group comprising visible light and infrared radiation). Hence, the system light comprises UV radiation (from the light source) and (a) visible radiation and/or (b) IR radiation of the luminescent material. Therefore, in embodiments system is configured generate system light having a total power (in Watt), wherein the system light comprises the light source radiation and the luminescent material radiation, wherein at least 2% of the total power is provided by the light source radiation and at least 2% of the total power is provided by (a) visible radiation and/or (b) IR radiation of the luminescent material, more especially, wherein at least 5% of the total power is provided by the light source radiation and at least 5% of the total power is provided by (a) visible radiation and/or (b) IR radiation of the luminescent material, even more especially wherein at least 10% of the total power is provided by the light source radiation and at least 10% of the total power is provided by (a) visible radiation and/or (b) IR radiation of the luminescent material.

The luminescent material radiation comprises in embodiments visible light. Hence, due to the presence of the luminescent material, the light generated by the system, includes both UV radiation and visible light. Hence, the system is configured to generate system light comprising the light source radiation and the luminescent material radiation. Luminescent materials that can absorb UV radiation and convert into visible radiation are known in the art, such as used in the art for mercury discharge lamps, plasma display panels, for UV LED applications, etc. Alternatively or additionally, the luminescent material radiation comprises infrared (IR) radiation. The infrared radiation may have a wavelength selected from the range of 780 nm-1 mm, such as 780 nm-15 µm, like 780 nm-8 µm, like 780 nm-3 µm.

As indicated above, in embodiments the system may further comprise an attenuation element, which is configured downstream of the light source and upstream of the luminescent material. The attenuation element may especially be configured to transmit part of the light source radiation, but may also be configured to reflect part of the light source radiation. At least part of the reflected light source radiation may be reused, by reflection in a waveguide element (assuming the availability of a waveguide element; see also below). As (in these embodiments) the luminescent material is configured downstream of the attenuation element, at least part of the luminescent material radiation that may impinge on the attenuation element may be reflected (and optionally part of the luminescent material radiation may also be transmitted by the attenuation element). With the attenuation element, it may be possible to get a more even distribution of the light source radiation over different directions and/or over a waveguide. The attenuation element may also be used to redirect at least part of the luminescent material radiation in a direction away of the attenuation element, of which otherwise a part might (in embodiments) be lost.

In embodiments, the attenuation element may be a layer of light reflective material, such as e.g. one or more of alumina, MgO, BaSO$_4$, etc., which may be used to reflect back part of the light source radiation (i.e. the light source radiation is generated at an upstream side of the attenuation element), and to transmit part of the light source radiation. The latter part may be used by the luminescent material that is configured downstream of the attenuation layer. Hence, the attenuation layer may thus also be used to reflect back part of the luminescent material radiation (i.e. the light source radiation is generated at an upstream side of the attenuation element). The attenuation layer may especially be a diffuse reflective layer.

In embodiments, the attenuation layer may be a particulate layer, e.g. comprising particulate material having a d50 selected from the range of 0.1-20 µm. Especially, at least 20 .wt % may consist of particles having particle sizes selected from the range of 0.1-1 µm. The particulate material may also have a size distribution with two maxima, such as a maximum based on particles with dimension in the range of the UV radiation and a maximum based on particles with dimensions in the range of visible (or IR) radiation. Further, the layer thickness may be chosen to transmit at least part of the light source radiation, e.g. a thickness selected from the range of 0.1-20 µm (this may depend upon the intensity of the light source and the desired purpose).

An example of an attenuation element may in embodiments be a semi-transparent mirror, which is transmissive for at least part of the light source radiation (generated upstream of the semi-transparent mirror) and which may be reflective for at least part of the luminescent material radiation (generated downstream of the semi-transparent mirror).

Herein, the invention is (further) especially explained (i) in relation to embodiments including the semi-transparent mirror and including luminescent material and (ii) in relation to embodiments including the luminescent material (and not including the semi-transparent mirror (or the attenuation element)).

As indicated above, in embodiments the system may further comprise a semi-transparent mirror configured downstream of the light source and upstream of the luminescent material. The term "semi-transparent mirror" may especially refer to an optical element that is at least partly transmissive for radiation with a first wavelength and is at least partly reflective for radiation with a second wavelength (different from the first wavelength). For such second wavelength, the optical element may essentially be non-transmissive. In the present context, the first wavelength may e.g. be a UV wavelength, and the second wavelength may be a wavelength in the visible and/or IR, and may thus in this context especially refer to luminescent material radiation. Note that the terms "first wavelength" and "second wavelength" may refer to a plurality of (different) first wavelengths, such as a wavelength range of first wavelengths, and a plurality of (different) second wavelengths, such as a wavelength range of second wavelengths, respectively.

For instance, the term "transmissive" and similar terms may refer to a transmission, especially under perpendicular radiation, of at least 10% of the radiation (having a first wavelength), especially at least 20%, such as at least 50%, whereas the term "non-transmissive" and similar terms may refer to a transmission, especially under perpendicular radiation, of less than 10%, such as less than 5% of the radiation (having a second wavelength). Further, for instance the term "reflective" and similar terms may refer to a reflection, especially under perpendicular radiation, of at least 10% of the radiation (having a first wavelength or having a second wavelength, respectively), especially at least 20%, such as at least 50%, like at least 80%.

Semi-transparent mirrors are known in the art. A semi-transparent mirror may e.g. be obtained with a thin layer of reflective material, such as a thin aluminum layer. Herein, the term "transmissive", and similar terms, especially in relation to the mirror, refer(s) to UV and visible radiation, and optionally to UV, visible and/or infrared radiation. Especially, herein the semi-transparent mirror is configured to transmit part of the UV radiation and to reflect at least part of the luminescent material radiation.

In embodiments, especially the percentage of radiation, under perpendicular radiation, of the luminescent material radiation that is reflected by the semi-transmissive mirror is larger than the percentage of the same luminescent material radiation that is transmitted through the semi-transmissive mirror.

Further, in embodiments, the percentage of radiation, under perpendicular radiation, of the light source radiation that is reflected by the semi-transmissive mirror is larger than the percentage of the same light source radiation that is transmitted through the semi-transmissive mirror. However, this is not necessarily the case. This may e.g. depend upon the desire intensity and/or on the number of light sources per area.

As indicated above, in embodiments the semi-transparent mirror may be an aluminum layer. The thickness thereof may e.g. be selected from the range of 4-50 nm, such as in the range of 4-30 nm, like 5-10 nm.

Instead of an integral layer that provides the semi-transparent mirror properties, also a layer may be applied that includes through holes. In such layer, which may also be indicated as patterned layer, part of the layer may consist of reflective material, and part of the layer may consist of through-holes in such reflective material. The thickness of a layer with hole may e.g. be selected from the range of 20-100 nm, such as in the range of 20-50 nm.

In embodiments, the semi-transparent mirror may be specular reflective, such as at least for rays (having a second wavelength) perpendicular to the semi-transparent mirror. In yet other embodiments, the semi-transparent mirror may be diffuse reflective, such as at least for rays (having a second wavelength) perpendicular to the semi-transparent mirror.

With the semi-transparent mirror, part of the UV radiation may escape to the external of the system. Further, the luminescent material generates luminescent material radiation. Hence, the system is especially configured to generate system light comprising the light source radiation (more especially at least UV radiation) and the luminescent material radiation.

UV radiation that is reflected (by the semi-transparent mirror (or attenuation element)) in the direction of the light source under a right angle, such as a solid state light source, may at least partly be lost. However, part of the light that is not reflected under a right angle may escape from the light source, such as a die of a solid state light source. Hence, with the invention it may be possible in embodiments to provide an emitter that emits in a first direction UV radiation and luminescent material radiation and emits in a second direction, perpendicular to the first direction, essentially only light source radiation, which may in embodiments be essentially UV radiation.

Assuming e.g. the use of a waveguide element, the light source radiation perpendicular to the first direction may be directed into the waveguide for propagation through the waveguide (see further also below). This may lead to escape of at least part of the this light source radiation elsewhere from the waveguide element (i.e. outcoupling from the waveguide element). Radiation that is (mainly) provided in the first direction may essentially directly escape from the waveguide and/or emanate from the waveguide in a direction perpendicular to the waveguide element (and perpendicular to the second direction). In this way, a more even intensity distribution of the UV radiation escaping from a radiation exit window of the waveguide element may be obtained.

Hence, in embodiments the light source, the semi-transparent mirror (or attenuation element), and the luminescent material are configured to provide at least part of the UV radiation in a direction perpendicular to the semi-transparent mirror and at least part of the UV radiation in a direction parallel to the semi-transparent mirror.

Above, the embodiment of a solid state light source is mentioned. Further aspects and embodiments of solid state light sources are also described below.

The solid state light source may comprise a die having a first face (or top face) and one or more side faces, which are configured under an angle with the top face. In embodiments, this angle may be selected from the range of 15-165°, such as selected from the angle of 30-150°, like selected from the angle of 45-135°. Especially, in embodiments the angle may essentially be 90°. As in embodiments light source radiation may escape from both the top face and from the one or more side face, radiation may escape from the die in a plurality of directions, amongst others directions perpendicular to each other. Hence, in embodiments such solid state light source may be applied to provide UV radiation in a direction perpendicular to the semi-transparent mirror and in a direction parallel to the semi-transparent mirror.

In embodiments, the system may comprise a package comprising a solid state light source. Therefore, in specific embodiments the system may comprise a solid state light source, wherein the solid state light source comprises a die, wherein the system comprises a package comprising the solid state light source. Especially, the solid state light source comprises a die that is able to provide light source radiation in a plurality of directions, especially include (also) two orthogonal directions. The package may at least partly be embedded in a waveguide element (see also below). In further specific embodiments, the packages is essentially entirely embedded in the waveguide element.

In embodiments, the package may further comprise the semi-transparent mirror. The semi-transparent mirror may be configured on the die. Hence, the semi-transparent mirror may be in physical contact with the die. The semi-transparent mirror may also be configured at a distance from the die, but in optical contact with the die. The semi-transparent mirror and the die may also sandwich a light transmissive layer, such as a light transmissive adhesive. The package may at least partly be embedded in a waveguide element (see also below). In further specific embodiments, the packages is essentially entirely embedded in the waveguide element.

In embodiments, the package may further comprise the luminescent material. The luminescent material may be configured on the semi-transparent mirror. Hence, the luminescent material may be in physical contact with the semi-transparent mirror. The luminescent material may also be configured at a distance from the semi-transparent mirror, but in optical contact with the semi-transparent mirror. The luminescent material and the semi-transparent mirror may also sandwich a light transmissive layer, such as a light transmissive adhesive. The luminescent material may especially be provided as luminescent material layer. Hence, the luminescent material layer may be in physical contact with the semi-transparent mirror. Therefore, in embodiments the luminescent material may be configured as luminescent material layer on the semi-transparent mirror. The luminescent material layer may also be configured at a distance from the semi-transparent mirror, but in optical contact with the semi-transparent mirror. The luminescent material layer and the semi-transparent mirror may also sandwich a light transmissive layer, such as a light transmissive adhesive. The package may at least partly be embedded in a waveguide element (see also below). In further specific embodiments, the packages is essentially entirely embedded in the waveguide element.

Especially, in embodiments the solid state light source may be part of a package together with the semi-transparent mirror and the luminescent material. Therefore, in specific embodiments the system may comprise a solid state light source, wherein the solid state light source comprises a die, wherein the system comprises a package (or "light generating package") comprising the solid state light source, the semi-transparent mirror, and the luminescent material, wherein the semi-transparent mirror is configured in optical contact with the die, and wherein the luminescent material is configured as luminescent material layer on the semi-transparent mirror.

The term "optical contact" and similar terms, such as "optically coupled" especially may mean that the light escaping from a first element may enter another (optical) second element with minimal losses (such as Fresnel reflection losses or TIR (total internal reflection) losses) due to refractive index differences of these elements. The losses may be minimized by one or more of the following elements: a direct optical contact between the two optical elements (i.e. physical contact), providing an optical glue between the two optical elements, preferably the optical glue having a refractive index higher that the lowest refractive index of the two individual optical elements, providing the two optical elements in close vicinity (e.g. at a distance (much) smaller than the wavelength of the radiation), such that the light will tunnel through the material present between the two optical elements, providing an optically transparent interface material between the two optical elements, preferably the optically transparent interface material having a refractive index higher that the lowest refractive index of the two individual optical elements, the optically transparent interface material might be a liquid or a gel or providing an optical Anti Reflection coating on the surfaces of (one or both of) the two individual optical elements. In embodiments, the optically transparent interface material may also be a solid material. Further, the optical interface material or glue especially may have a refractive index not higher than the highest refractive index of the two individual optical elements.

Instead of the term "in optical contact" also the terms "radiationally coupled" or "radiatively coupled" may be used. The term "radiationally coupled" especially means that the respective elements are associated with each other so that at least part of the radiation emitted by the first element is received by the second element. The elements may in embodiments be in physical contact with each other or may in other embodiments be separated from each other with a (thin) layer of optical glue, e.g. having a thickness of less than about 1 mm, preferably less than 100 μm. When no optically transparent interface material is applied, the distance between two elements being in optical contact may especially be about at maximum the wavelength of relevance, such as the peak wavelength of a solid state light source. For visible wavelengths, this may be less than 1 μm, such as less than 0.7 μm, and for blue even smaller, such as less than about 400 nm.

In specific embodiments, the system may essentially consist of the package, such as a LED package including the semi-transparent mirror and the luminescent material. In yet other embodiments, the system may comprise a plurality of packages (see also below). In yet further embodiments, the system may comprise a plurality of light sources and a single semi-transparent mirror (see also further below). Hence, effectively, in an aspect the invention is also directed to such package per se.

Especially, the system comprises a sheet-like light output device. With such sheet-like device, (large) areas of an object can be irradiation or (large) objects can be coated with the sheet-like device. In this way, the sheet-like device can be a second skin of the object. The sheet-like device may be flat. However, in other embodiments the sheet-like device may also be curved. Hence, the light emitting area of light emissive surface of the sheet-like light output device may be flat or may be one-dimensionally or two-dimensionally curved. Hence, in embodiments the UV emitting element may comprise such sheet-like light output device. The term "sheet-like" may refer to a panel, such as a thin panel, which may in embodiments be flexible or in embodiments be inflexible, especially flexible. The term "sheet-like" may refer to a flexible sheet. For instance, a sheet of silicone may be relatively flexible and may form a second skin of the object. However, would e.g. quartz be used, the sheet-like device may be relatively inflexible.

The light emissive surface area of such sheet-like light output device may have any dimension, but may especially relatively large, such as at least 9 cm$^2$, like at least 16 cm$^2$, such as at least 25 cm$^2$. Hence, in embodiments the sheet-like light output device may have a light emissive surface of at least 100 cm$^2$, like at least 400 cm$^2$. However, larger may also be possible, such as a sheet-like light output device having a light emissive surface of at least 2500 cm$^2$, or even at least 1 m$^2$. Substantially larger may also be possible, such as when sheet-like light output devices are generated via e.g. a roll-to-roll process.

With the luminescent material, it is possible to tune the intensity of the UV radiation escaping from a surface of the system, such as the light emissive surface of a sheet-like light output device. Hence, in embodiments with the luminescent material the UV radiation escaping from a waveguide, such as via a radiation exit window thereof, may be tuned.

The luminescent material may be configured at different positions while having the same effect. In embodiments, the luminescent material may be configured downstream of a light emissive surface, such as a radiation exit window of a waveguide. In embodiments wherein the light source radiation may only escape from the lighting system only after one or more (total internal) reflections, such as in the case of a waveguide, the luminescent material may also be configured elsewhere, such as within the waveguide, or at a back side of the waveguide.

In embodiments, the luminescent material may be configured within the waveguide. Hence, luminescent material radiation and anti-biofouling light may escape from the radiation exit window. In such embodiments, the light emissive surface may essentially be identical with the radiation exit window; the radiation exit window is especially a face of the waveguide or the face. Alternatively or additionally, the luminescent material may in embodiments be configured on (part of) the radiation exit window. Luminescent material radiation may escape from the luminescent material and anti-biofouling light may escape through the luminescent material (when the layer of luminescent material is (locally) thin enough and/are from the radiation exit window where no luminescent material is available. In such embodiments, the light emissive surface may comprise the layer of luminescent material and/or the radiation exit window, respectively.

Whatever option(s) is (are) chosen, the system is especially configured to radiate (in an operation mode) part of the light source radiation to the exterior of the sheet-like light output device via the light emissive surface with a predetermined dose of at least 10 J/m$^2$, relative to the light emissive surface, like in the range 100-3000 J/m$^2$ Alternatively or additionally, the system is especially configured to radiate (in an operation mode) part of the light source radiation to the exterior of the sheet-like light output device via the light emissive surface with a predetermined average power over time, such as an average power over time of at least about 0.5*10$^{-9}$ Watt/mm$^2$, like at least about 10$^{-9}$ Watt/mm$^2$, such as at least about 1.5*10$^{-9}$ Watt/mm$^2$, relative to the area of the light emissive surface, like no more than 10$^{-6}$ Watt/mm$^2$, such as no more than 0.5*10$^{-7}$ Watt/mm$^2$, like no more than 10$^{-7}$ Watt/mm$^2$. Therefore, in embodiments the system may be configured to radiate in an operation mode part of the light source radiation (to in specific embodiments the exterior of a sheet-like light output device) via a light emissive surface with an average power over time of at least 0.5×10$^{-9}$ Watt/mm$^2$, averaged over the light emissive surface. Hence, the phrase "power, relative to the area" or "power over time, relative to the area" and similar phrases, especially indicate that the relevant parameter is averaged over the area, such that an average value of the relevant parameter (such as the power over time in Watt/mm$^2$) is obtained.

As indicated herein, the system may execute an action in a "mode" or "operation mode" or "mode of operation". The term "mode" may also be indicated as "controlling mode". This does not exclude that the system may also be adapted for providing another controlling mode, or a plurality of other controlling modes. However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system that can only operate in a single operation mode (i.e. "on", without further tenability).

In an embodiment, in an operation mode the light source radiation is provided continuously. In yet another embodiment, in an operation mode the light source radiation is provided in a pulsed way. In yet another embodiment, in an operation mode the light source radiation is provided in dependence of a sensor signal, such as from a sensor configured to sense biofouling. In yet another embodiment, the light source radiation is provided upon instruction via a user interface. In embodiments, two or more of these embodiments are provided (by the system). Hence, as also indicated below the invention also provides a method of controlling the system (as described herein).

As indicated above, the system may especially comprise a waveguide. One or more light sources external from the waveguide and/or one or more light sources embedded in the waveguide may provide the light source radiation to the waveguide. By total internal reflection, at least part of the light source radiation may be distributed over the waveguide and escape from a radiation exit window thereof. A waveguide may be comprised by a sheet-like light output device. Hence, in embodiments the system comprises a waveguide element arrangement, wherein the waveguide element arrangement comprises a waveguide element comprising a radiation exit window, wherein the waveguide element is (a) configured to receive the light source radiation, and (b) configured to radiate (in an operation mode) part of the light source radiation to the exterior of the waveguide element via the radiation exit window, and wherein the waveguide element arrangement further comprises a converter arrangement comprising the luminescent material. Instead of the term "waveguide element" also the term UV-emitting element may be used. Especially, the waveguide element is configured to provide, during use of the system, UV radiation. The term "waveguide element" may especially refer to a waveguide and optionally other elements embedded therein, such as a light source, or configured thereon, such as a luminescent material (layer).

In specific embodiments, the light source may be embedded in the waveguide element. Hence, a single light source with a single light emitting surface, a single light source with a plurality of light emitting surfaces (such as fiber tips of a plurality of fibers), or a plurality of light sources with a plurality of light emitting surfaces (such as a plurality of LEDs (with the LED dies providing the light emitting surfaces) may be embedded in the waveguide element, i.e. especially embedded in the waveguide material, such as e.g. silicone. Hence, the waveguide element especially comprises waveguide material. The light source(s) may be (at least partly) embedded in the waveguide material. Light source radiation may propagate through the waveguide material and escape from the waveguide material via the radiation exit window. Part of the waveguided UV light may be scattered inside the waveguide (e.g. by the silicone) and arrive the radiation exit window under angles steep enough to leave the waveguide (and enables anti fouling). In embodiments, part of the light source radiation may also directly escape from the waveguide (and e.g. meet luminescent material). In alternative embodiments, the light source may be partly embedded in the waveguide element. Hence, in embodiments the light source may at least partly be embedded in the waveguide element.

Hence, to promote outcoupling of light from the waveguide element, such as light source radiation (and/or luminescent material radiation in some embodiments), the waveguide material may comprise outcoupling structures, such as scattering elements in the waveguide material or outcoupling structures in the radiation exit window, like roughness, and/or on the radiation exit window. Scattering element may include particulate material that is embedded in the waveguide element, such as scattering elements embedded in the silicone.

This converter arrangement may refer to one or more of luminescent materials configured on the radiation exit window, configured further away from the radiation exit window (and also downstream thereof)(such as e.g. a layer at some distance of the radiation exit window), configured within the waveguide element, configured at a face opposite of the radiation exit window (with waveguide material configured between the radiation exit window and the face opposite thereof), etc.

In embodiments, the luminescent material may be configured on the waveguide element. Alternatively or additionally, the luminescent material may be configured within the waveguide element. Alternatively or additionally, the luminescent material may (even) be configured remote from the waveguide element.

In specific embodiments, a waveguide element may be applied that is configured between the light source and the semi-transparent mirror. For instance, on a (downstream) face of the waveguide element, the semi-transparent mirror may be configured, with the luminescent material configured downstream of the semi-transparent mirror, such as a layer (or a patterned layer).

In yet other embodiments, a waveguide element may be applied that is configured downstream of the semi-transparent mirror. For instance, the light source may be configured upstream of the semi-transparent mirror, such as in physical contact with the semi-transparent mirror and the waveguide element may be configured downstream of the semi-transparent mirror, such as in physical contact therewith. On a (downstream) face of the waveguide element, the luminescent material may be configured such as a layer (or a patterned layer). The semi-transparent mirror may be provided at an upstream face of the waveguide element.

Hence, in embodiments the semi-transparent mirror may be configured downstream of the waveguide element and upstream of the luminescent material. Therefore, in specific embodiments the semi-transparent mirror is configured downstream of the waveguide element and upstream of the converter arrangement (comprising the luminescent material).

Above, embodiments of a package, such as especially including a solid state light source, are described. Such package may also be combined with a waveguide element. For instance, one or more packages may be configured partly upstream of the waveguide element. As the UV radiation that is directed in a (second) direction should enter the waveguide, it is desirable that the die of the solid state light source is at least partly embedded in the waveguide element. Hence, in specific embodiments the system may comprise one or more packages, especially a plurality of the packages, wherein one or more packages, especially each package, is configured at least partly embedded in the waveguide element.

When the light source is at least partly embedded in the waveguide element, the light source may provide light source light in different directions, such as a first direction perpendicular to a top surface of a die and in a second direction perpendicular to the first direction and perpendicular to an edge face of the die. The die of a solid state light source may have a height of e.g. about 200-500 µm. Such solid state light source, the light thereof may be used in the first direction for providing UV radiation, of which part may be converted by the luminescent material, and in a second direction, e.g. for distribution of the waveguide element and escape therefrom as UV radiation elsewhere. This UV radiation may be used as such or may be (at least partly) converted by luminescent material, when available at the location (of downstream thereof) where the UV radiation escapes from the waveguide element. With solid state light sources with dies emitting in a plurality of directions, including emission from a top face of the die and emission from a side face of the die, both radiations may usefully be used in the waveguide element. Especially, solid state light sources may be applied wherein about 10-90% of the light source radiation escapes from a top face, such as 50-80%, and 90-10% of the radiation escapes from one or more side faces, such as 20-50%. Hence, especially a solid state light source is applied that may e.g. be a top emitter that has also emission at a side.

To provide solid state light sources with an attenuation element and/or a semi-transparent mirror on the die, one may provide a substrate with a plurality of solid state light source dies, apply (such as by coating) the attenuation element and/or semi-transparent mirror on the dies, and create solid state light source packages of one or more solid state light source dies including the attenuation element and/or semi-transparent mirror on the dies, such as by dicing. Likewise, to provide solid state light sources with (i) an attenuation element and/or a semi-transparent mirror on the die, and (ii) luminescent material on the attenuation element or a semi-transparent mirror, one may provide a substrate with a plurality of solid state light source dies, apply (such as by coating) (i) the attenuation element and/or semi-transparent mirror on the dies, (ii) the luminescent material (or a precursor thereof followed by conversion to the luminescent material) thereon, and create solid state light source packages of one or more solid state light source dies including (a) the attenuation element and/or semi-transparent mirror on the dies, and (b) the luminescent material on the attenuation element or semi-transparent mirror, such as by dicing.

Especially, the system is configured to radiate (in an operation mode) part of the light source radiation to the exterior of the waveguide element via the radiation exit window with an average power over time of at least 2 $mW/h/m^2$, relative to the radiation exit window.

In embodiments, an average dose (of the UV radiation) over time is selected from the range of at least 10 $J/m^2$, like especially selected from the range of 100-3000 $J/m^2$.

Alternatively or additionally, the system is configured to radiate (in an operation mode) part of the light source radiation to the exterior of the waveguide element via the radiation exit window with an average power over time of at least about $0.5*10^{-9}$ Watt/$mm^2$, like at least about $10^{-9}$ Watt/$mm^2$, such as at least about $1.5*10^{-9}$ Watt/$mm^2$, relative to the radiation exit window, like no more than $10^{-6}$ Watt/$mm^2$, such as no more than $0.5*10^{-7}$ Watt/$mm^2$, like no more than $10^{-7}$ Watt/$m^2$.

Especially, such waveguide element in combination with the converter element allows evening the intensity of the light source radiation that escapes from the light emissive surface. For instance, luminescent material may especially be configured at those locations of the waveguide where the likelihood of rays of the light source radiation escaping from the waveguide is relatively large. Less or no luminescent material may be configured at other locations.

Hence, in embodiments the light source and the converter arrangement are configured such that a local maximum value (especially essentially all local maximum values) of the power of the light source radiation escaping from the light emissive surface is (are) at maximum 20 times, such as at maximum 15 times, like at maximum 5 times, such as at maximum 2 times, like at maximum 1.5 times, equal to or larger than an average value of the power of the light source radiation averaged over the light emissive surface. In this way, intensity spots with too much light source radiation are prevented and absorbed and at least partly converted into useful luminescence. At the same time, the overall light source radiation escaping from the sheet-like light output device or waveguide element arrangement is evened out.

Other local minima or maxima may thus deviate less from the (over the light emissive surface) averaged value of the power of the light source radiation.

Therefore in (further) embodiments, the system may be configured to radiate in an operation mode part of the light source radiation to the exterior of the waveguide element with a first average value of the power (over time), relative to the light emissive surface, wherein the light source and the converter arrangement are configured such that a local maximum value (especially essentially all local maximum values) of the power of the light source radiation escaping from the light emissive surface is (are) at maximum 20 times, such as at maximum 15 times, like at maximum 5 times, such as at maximum 2 times, like at maximum 1.5 times larger than the first average value of the power of the light source radiation averaged over the light emissive surface. As indicated herein, the light emissive surface especially comprises the radiation exit window.

Hence, in embodiments also a local minimum value (especially essentially all local minimum values) of the power of the light source radiation escaping from the light emissive surface is (are) at maximum 20 times, such as at maximum 15 times, like at maximum 5 times, such as at maximum 2 times, like at maximum 1.5 times, smaller than an average value of the power of the light source radiation averaged over the light emissive surface.

The luminescent material may thus not be evenly distributed. For instance, the luminescent material may be available as pattern just upstream or downstream of the radiation exit window of a waveguide. For instance, the luminescent material can be deposited on top of the waveguide, such as a silicone layer, by printing or coating and/or patterning. Alternatively or additionally, it might also be realized by adding the luminescent material in the top area of the casted waveguide material, such as silicone, for example by in-mold deposition. Therefore, in embodiments the converter arrangement comprises a pattern of luminescent material on the radiation exit window. Especially, the pattern of luminescent material is especially configured to reduce intensity differences of light source radiation over the light emissive surface. Hence, the differences between local maxima (and minima) and an average power value, may be evened out with the pattern of luminescent material, e.g. on the radiation exit window.

Such pattern may be configured such that it reduces an uneven distribution of the light source radiation escaping from the system, such as escaping from the UV emitting element or sheet-like light output device. For instance, when the UV emitting element includes a plurality of light emitting surfaces, the pattern may be configured such, that local maxima of the UV radiation are reduced, whereas local minima are only partly or substantially not reduced. Hence, in embodiments, the light source may comprise a plurality of light emitting surfaces, wherein the light source is configured to provide the light source radiation via the plurality of light emitting surfaces. Especially, in such embodiments the light emitting surfaces may be configured in a 2D light emitting surfaces array. Especially, in such embodiments the converter arrangement may comprise a 2D converter array with a plurality of first areas with the luminescent material and one or more second areas with no or less luminescent material, wherein the 2D converter array is aligned with the light emitting surfaces array. Alignment may especially indicate that the light source radiation is reduced such that the difference between local maxima of light source radiation escaping from the system do not deviate too much from an average intensity and/or such that the difference between local minima of the light source radiation escaping from the system do not deviate too much from an average intensity. Hence, especially during operation the first areas may receive more light source radiation in watt/mm$^2$ than adjacent second areas.

Such areas may thus be provided in a 2D converter array. The areas themselves may also be patterned, such that in embodiments not all UV radiation is blocked. Hence, in embodiments one or more of (i) one or more of the plurality of the first areas and (ii) one or more of the one or more second areas are patterned. In specific embodiments, one or more of the plurality of the first areas are patterned.

The term "pattern" may especially refer to a regular or irregular arrangement or a combination of a regular and irregular arrangement of areas of luminescent material and areas without luminescent material.

The term "pattern" may include a continuous layer, such as on the radiation exit window, of luminescent material, wherein such layer includes through holes. The holes form a kind of discontinuous layer. The holes are islands and may form a regular and/or irregular arrangement.

The term "pattern" may include a virtual continuous layer of no (luminescent material), such as on the radiation exit window, wherein such virtual layer includes through holes which are filled with luminescent materials. The luminescent material is configured as island, which may form a regular and/or irregular arrangement.

For instance, the luminescent material may be coated and/or printed on the radiation exit window.

As indicated above, when a plurality of light sources is applied, in embodiments two or more light sources may be independently controlled. This allows a control of the spatial distribution of the beam. However, this may also allow a control of the (local) spectral distribution of the system light when also different luminescent materials are applied (which have different spectral distributions of their luminescent material radiation). In this way, also the spectral distribution of the system light may be controlled. This may be used to adapt the color of the light to the remainder of the color of the object, such as of material surrounding a sheet-like light output device. It may also be used to generate patterns, text messages, logos, etc. etc. Hence, in embodiments the system may comprise a plurality of light sources of which two or more subsets of light sources are independently controllable, wherein the system further comprises a plurality of different luminescent materials having different spectral distributions of the luminescent material radiation, wherein different combinations of subsets of light sources and luminescent materials are configured to provide the different spectral distributions of the luminescent material radiation, wherein the system further comprises a control system configured to control the plurality of light sources for controlling one or more of the spectral distribution of the system light and the spatial distribution of the system light.

Hence, in embodiments the system may comprise a plurality of controllable light sources and a plurality of different luminescent materials having different spectral distributions of the luminescent material radiation, wherein the different luminescent material are optically coupled to different controllable light sources, wherein the system further comprises a control system configured to control the plurality of light sources for controlling one or more of the spectral distribution of the system light and the spatial distribution of the system light.

In embodiments, one may use different light sources that preferentially excite a specific type of luminescent materials. Alternatively or additionally, the different luminescent material may be arranged at spatially different positions, such that spatially differently arranged light sources may excite the at spatially different positions arranged luminescent materials, respectively. For instance, the different luminescent materials may be provided in a (regular) pattern. Such pattern may correspond to a light distribution of the light sources.

In yet a further aspect, the invention also provides a computer program product, when running on a computer which is functionally coupled to or comprised by the system as defined herein, is configured to control the light source. This may thus also imply that a plurality of light sources is controlled. In this way, the spatial distribution of the light source radiation, such as escaping from a light emissive surface may be controlled. Alternatively or additionally, the spectral distribution of the luminescent material radiation may be controlled, especially when a plurality of light sources and a plurality of different luminescent materials is applied. When the different luminescent materials are radiationally coupled to different light sources, the spectral distribution may be controlled. In embodiments the intensity of the system light may be controlled. Controlling may be done according to one or more of a sensor signal of a sensor, a timer, etc. Hence, the system may further comprise one or more sensors which may be configured to sense one or more of biofouling, temperature, contact of part of the system, such as especially the light emissive surface with water, human or animal proximity to the system, such as especially the light emissive surface, etc. etc.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element.

The controlling of the element can be done with a control system. The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems.

Below, possible aspects of the invention are discussed in more detail.

As indicated above, the anti-biofouling system comprises a UV-emitting element. The term "UV-emitting element" may also refer to a plurality of UV-emitting elements. Hence, the system may include a plurality of such elements. The system may include a source of electrical energy, but the system may (during use) also be functionally coupled with a source of electrical energy. In embodiments, each UV-emitting element may functionally be coupled with a source of energy. This allows a decentral powering of the UV-emitting elements. The source of energy is especially used for powering the light source(s).

Herein, the UV-emitting element can also be indicated as "lighting module". The UV-emitting element may be a plate-like module (herein also indicated as "optical medium"), with one or more relevant elements at least partly, or even entirely, embedded therein. Hence, in embodiments the UV-emitting element comprises light transmissive (solid) material, such as silicone, etc. However, the UV element may also include a housing enclosing at least partly, or even entirely, one or more relevant elements. The one or more relevant elements at least comprise the light source, which is configured to provide light source radiation, especially the UV radiation. The UV-emitting element may have a flat or a curved radiation exit window. The term "UV-emitting element" indicates that the element is especially configured to provide UV radiation during use of the element.

The waveguide element may be shaped as a plate, optionally a curved shape. However, the waveguide element may also have other shapes. This may depend e.g. from the application. For instance, when the object is a door knob, a tap knob, a toilet knob, a railing, a kitchen cutting board, or a medical device, the shape of the waveguide element may be or need to be different than a plate, and may have one or more curved faces.

As the waveguide element may be planar, the light sources may be configured such, that the optical axis is substantially parallel to a length axis of the waveguide element. This may facilitate distribution of the light source radiation over the waveguide. For instance, the light source may include a side emitting LED. Especially, the waveguide element may include a plurality of side emitting LEDs.

The UV-emitting element comprises a UV radiation exit window. The UV radiation exit window is configured to transmit at least part of the UV radiation of the light source. At least part of the UV radiation escapes via the radiation exit window to the exterior of the UV-emitting element. Hence, the exit window is transmissive for UV radiation. In general, the window will also be transmissive for visible light. As indicated above, and as will further be explained below, in embodiments the element may be a radiation transmissive plate. In such instance, the window may be a face (or plane) of the element.

The term "radiation transmissive" refers to transmissive for radiation, especially for UV radiation and optionally also for visible radiation.

The UV radiation exit window comprises an upstream window side and a downstream window side. The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream". Hence, the upstream window side ("upstream side") is especially directed to the internal of the element and may receive, directly, or after internal reflection, light source radiation. The downstream window side ("downstream side") may especially be directed to the exterior of the element. This window side may e.g. (temporarily) be in contact with water during use of the system. Note that in plate-like embodiments of the element the upstream window side and a downstream window side may be both sides of the (same) edge (or plane).

As indicated above, especially the object, or the anti-biofouling system, may further comprise a control system. Hence, the object may comprise such control system. In embodiments the anti-biofouling system comprises the control system, but external from the object. Therefore, in embodiments the anti-biofouling system may further comprise a control system, optionally enclosed by the UV-emitting element. When the control system comprises more than one element, one or more elements may be comprised by the object and/or one or more elements may be configured external from the object.

In an embodiment, the control system comprises a plurality of control systems. For instance, the vessel may comprise a control system, as master control system, with each anti-biofouling system comprising a slave control system. Optionally, the control system may be configured external from the object, i.e. remote from the object. In specific embodiments, a master control system, remote from the object, controls the slave control system comprised by the object, (such as the anti-biofouling system). Hence, for instance the (master) control system may be far away; or not on the vessel, but ashore, such as in a control room of a shipping company. Such master control system may be configured to control anti-biofouling.

Especially, the system comprises a plurality of UV light sources. Even more especially, these may essentially be arranged in a regular pattern.

Hence, in embodiments the anti-biofouling system comprises a plurality of light sources, wherein neighboring light sources have mutual light source distances (d1) selected from the range of 0.5-200 mm, such as 2-100 mm In yet further embodiments, the biofouling system comprises a plurality of LEDs, wherein the LEDs are configured to generate said UV radiation, wherein the LEDs comprise LED dies, and wherein the LED dies of neighboring LEDs have mutual light source distances (d1) selected from the range of 0.5-200 mm, As already indicated above, the system may also comprise a plurality of light sources, wherein each light source is primarily directed to part of the radiation exit window.

Hence, especially the system is an anti-biofouling system. In embodiments, the anti-biofouling system comprises a waveguide element, such as a sheet-like light output device, wherein in further specific embodiments the light sources are embedded in the waveguide element. Especially, the waveguide element is watertight. Herein, the term "watertight" may in specific embodiments refer to International Protection Marking IPx5 or higher, such as IPx6, like especially IPx7 (immersion, up to 1 m depth), even more especially IPx8 (immersion, 1 m or more depth). The value of x is especially at least 4, like at least 5, such as 6.

As indicated above, in a further aspect the invention provides an object comprising the system as defined herein, wherein the system is configured to irradiate with radiation during an irradiation stage one or more of (i) a part of an external surface of said object and (ii) water adjacent to said part of said external surface. In yet a further aspect, the invention provides an object comprising the system as defined herein, wherein the system comprises a waveguide element, wherein the waveguide element is configured to irradiate with radiation during an irradiation stage one or more of (i) a part of an external surface of said object and (ii) water adjacent to said part of said external surface.

Especially, the object may be an object that during use is at least partly submerged in water. Hence, the object may comprising the anti-biofouling system as defined herein, wherein the UV-emitting element is configured to irradiate with UV radiation during an irradiation stage one or more of (i) a part of an external surface of said object and (ii) water adjacent to said part of said external surface. As indicated above, the object may especially be selected from the group consisting of a vessel and an infrastructural object.

Herein, the phrase "object that during use is at least partly submerged in water" and similar phrases may especially refer to objects such as vessels and infrastructural objects that have aquatic applications. Therefore, in embodiments the object may be configured to be at least partly submerged in water during use.

Hence, during use such object will be in general in contact with the water, like a vessel in the sea, a lake, a canal, a river, or another waterway, etc. The term "vessel" may e.g. refer to e.g. a boat or a ship, etc., such as a sail boat, a tanker, a cruise ship, a yacht, a ferry, a submarine, etc. etc. The term "infrastructural object" may especially refer to aquatic applications that are in general arranged substantially stationary, such as a dam, a sluice, a pontoon, an oilrig, etc. etc. The term "infrastructural object" may also refer pipes (for e.g. pumping up ocean water to e.g. a power plant), and other parts of (hydro-electrical) power plants, such as cooling systems, turbines, etc. The term "infrastructural object" may also refer to an oil rig. The term "infrastructural object" may also refer to a structure for harvesting tidal energy and/or for harvesting wave energy and/or for harvesting ocean current derived energy, etc.

The term "external surface" especially refers to the surface that may be in physical contact with water. In the case of pipes this may apply to one or more of the internal pipe surface and the external pipe surface. Hence, instead of the term "external surface" also the term "fouling surface" may be applied. Further, in such embodiments the term "water line" may also refer to e.g. filling level. Especially, the object is an object configured for aquatic (such as marine) applications, i.e. application in or near to a sea or an ocean. Such objects are during their use at least temporarily, or substantially always, at least partly in contact with the water. The object may be at least partly below the water (line) during use, or may substantially be all of its time below the water (line), such as for submarine applications. The invention may e.g. be applied for aquatic (such as marine) anti-fouling, keeping wetted surfaces clean, for off-shore applications, for (sub) sea applications, for drilling platforms, etc.

Due to this contact with the water, biofouling may occur, with the above indicated disadvantages. Biofouling will occur at the surface of an external surface ("surface) of such object. The surface of an (element of the) object to be protected may comprise steel, but may optionally also comprise another material, such as e.g. selected from the group consisting of wood, polyester, composite, aluminum, rubber, hypalon, PVC, glass fiber, etc. Hence, instead of a steel hull, the hull may also be a PVC hull or a polyester hull, etc. Instead of steel, also another iron material, such as an (other) iron alloys may be used Herein, the term "fouling" or "biofouling" or "biological fouling" are interchangeably used. Above, some examples of fouling are provided. Biofouling may occur on any surface in water, or close to water and being temporarily exposed to water (or another electrically conductive aqueous liquid). On such surface biofouling may occur when the element is in, or near water, such as (just) above the water line (like e.g. due to splashing water, such as for instance due to a bow wave). Between the tropics, biofouling may occur within hours. Even at moderate temperatures, the first (stages of) fouling will occur within hours; as a first (molecular) level of sugars and bacteria.

The anti-biofouling system comprises at least an UV-emitting element. Further, the anti-biofouling system may comprise a control system (see also below), an electrical energy supply, etc.

The term "anti-biofouling system" may also refer to a plurality of such systems, optionally functionally coupled to each other, such as e.g. controlled via a single control system. Further, the anti-biofouling system may comprise a plurality of such UV-emitting elements. Herein, the term "UV-emitting element" may (thus) refer to a plurality of UV-emitting elements. For instance, in an embodiment a plurality of UV-emitting elements may be associated to an external surface of the object, such as a hull, or may be comprised by such surface (see also below), whereas e.g. a control system may be configured somewhere within the object, such as in a control room or wheel house of a vessel.

The surface or area on which fouling may be generated is herein also indicated as fouling surface. It may e.g. be the hull of a ship and/or an emission surface of an optical medium (see also below). To this end, the UV-emitting element provides UV radiation (anti-fouling light) that is applied to prevent formation of biofouling and/or to remove biofouling. This UV radiation (anti-fouling light) especially at least comprises UV radiation (also indicated as "UV light"). Hence, the UV-emitting element is especially configured to provide UV radiation. Thereto, the UV-emitting element comprises a light source. The term "light source" may also relate to a plurality of light sources, such as 2-2000 (solid state) LED light sources, though many more light sources may also be applied. Hence, the term LED may also refer to a plurality of LEDs. Especially, the UV-emitting element may comprise a plurality of light sources. Hence, as indicated above, the UV-emitting element comprises one or more (solid state) state light sources. The LEDs may be (OLEDs or) solid state LEDs (or a combination of these LEDs). Especially, the light source comprises solid state LEDs. Hence, especially, the light source comprises a UV LED configured to provide one or more of UV-A, UV-B, and UVC light (see also below). UV-A may be used to impair cell walls, whereas UVC may be used to impair DNA. Hence, the light source is especially configured to provide the UV radiation. Herein, the term "light source" especially refers to a solid state light source. The light source(s) may also include (a) solid state laser(s). The term "light source" may also refer to a light source including optics, such as a solid state light source with one or more beam shaping elements selected from the group of a lens and a reflector (such as a collimator).

The solid state light source, such as a LED, may be a top-emitter or a side emitter. In embodiments, the light source light of the LED is emitted in at least two perpendicular directions, such as from the top and from a side of the LED die (see also above).

Especially, the light source or the light sources is (are) LEDs. Hence, in embodiments the anti-biofouling system comprises a plurality of light sources, wherein the light sources comprise LEDs. Alternatively or additionally, the light sources comprise solid state lasers. Alternatively or additionally, the light source comprises nano wires or nano pyramids, such as e.g. described above.

Ultraviolet (UV) is that part of electromagnetic light bounded by the lower wavelength extreme of the visible spectrum and the X-ray radiation band. The spectral range of UV light is, by definition between about 100 and 400 nm (1 nm=$10^{-9}$ m) and is invisible to human eyes. Using the CIE classification the UV spectrum is subdivided into three bands: UVA (long-wave) from 315 to 400 nm; UVB (medium-wave) from 280 to 315 nm; and UVC (short-wave) from 100 to 280 nm. In reality many photobiologists often speak of skin effects resulting from UV exposure as the weighted effect of wavelength above and below 320 nm, hence offering an alternative definition.

In embodiments the UV radiation (anti-fouling light) comprises UVC light. In embodiments, the UV radiation comprises radiation selected from a wavelength range of 100-300 nm, especially 200-300 nm, such as 230-300 nm. Hence, the UV radiation may especially be selected from UVC and other UV radiation up to a wavelength of about 300 nm. Good results are obtained with wavelengths within the range of 100-300 nm, such as 200-300 nm.

As indicated above, in embodiments the UV-emitting element may be configured to irradiate with said UV radiation (during an irradiation stage) one or more of (i) said part of said external surface and (ii) water adjacent to said part of said external surface. The term "part" refers to part of the external surface of an object, such as e.g. a hull or a sluice (door). However the term "part" may also refer to substantially the entire external surface, such as the external surface of the hull or sluice. Especially, the external surface may comprise a plurality of parts, which may be irradiated with the UV light of one or more light sources, or which may be irradiated with the UV radiation of one or more UV-emitting elements. Each UV-emitting element may irradiate one or more parts. Further, there may optionally be parts that receive UV radiation of two or more UV-emitting elements.

In general, especially when referring to aquatic (such as marine) applications, there may be distinguished between two main embodiments. One of the embodiments includes the part of the external surface being irradiated with the UV radiation with between the light source and UV-emitting element water (or air when above the water line), such as sea water, at least during the irradiation stage. In such embodiment, the part is especially comprised by the "original" external surface of the object. However, in yet another embodiment, the "original" external surface may be extended with a module, especially a relatively flat module, that is attached to the "original" external surface of the object (such as the hull of a vessel), whereby the module itself forms in fact the external surface. For instance, such module may be associated to the hull of a vessel, whereby the module forms (at least part of) the external surface. In both embodiments the UV-emitting element especially comprises a radiating exit surface (see further also below). However, especially in the latter embodiment wherein the UV-emitting element may provide part of said external surface, such radiation exit window may provide the part (as the first part and the radiation exit window may essentially coincide; especially may be the same surface).

Hence, in an embodiment the UV-emitting element is attached to said external surface. In yet a further specific embodiment the radiation exit window of the anti-biofouling system is configured as part of said external surface. Hence, in some of the embodiments the object may comprise a vessel comprising a hull, and the UV-emitting element is attached to said hull. The term "radiation exit window" may also refer to a plurality of radiation exit windows (see also below).

In both general embodiments, the UV-emitting element is configured to irradiate with said UV radiation (during an irradiation stage) water adjacent to said part of said external surface. In the embodiments wherein the module itself forms in fact the external surface, the UV-emitting element is at least configured to irradiate with said UV radiation (during an irradiation stage) said part of said external surface, as it is in fact part of said external surface, and optionally also water adjacent to said part of said external surface. Hereby, biofouling may be prevented and/or reduced.

In an embodiment, a significant amount of a protected surface to be kept clean from fouling, preferably the entire protected surface, e.g. the hull of a ship, may be covered with a layer that emits germicidal light ("anti-fouling light"), in particular UV light.

In yet another embodiment, the UV radiation (anti-fouling light) may be provided to the surface to be protected via a waveguide, such as a fiber.

Hence, in an embodiment the anti-fouling lighting system may comprise an optical medium, wherein the optical medium comprises a waveguide, such as an optical fiber, configured to provide said UV radiation (anti-fouling light) to the fouling surface. The surface of e.g. the waveguide from which the UV radiation (anti-fouling light) escapes is herein also indicated as emission surface. In general, this part of the waveguide may at least temporarily be submerged. Due to the UV radiation (anti-fouling light) escaping from the emission surface, an element of the object that is during use at least temporarily exposed to the liquid (such as seawater), may be irradiated, and thereby anti-fouled. However, the emission surface per se may also be anti-fouled. This effect is used in some of the embodiments of the UV-emitting element comprising an optical medium described below.

Embodiments with optical media are also described in WO2014188347. The embodiments in WO2014188347 are herein also incorporated by reference as they are combinable with the control unit and/or water switch, and other embodiments, described herein.

As indicated above, the invention may also be applied for other applications than aquatic (such as marine) applications, like for (door) knobs, hospital curtains, or other medical and non-medical applications, etc.

As indicated above, the UV-emitting element may especially comprise a UV radiation exit window. Hence, in a specific embodiment the UV-emitting element comprises a UV radiation exit window, with the UV-emitting element especially being configured to provide said UV radiation downstream from said UV radiation exit window of said UV-emitting element. Such UV radiation exit window may be an optical window through which the radiation escapes from the UV-emitting element. Alternatively or additionally, the UV radiation exit window may be the surface of a waveguide. Hence, UV radiation may be coupled in the UV-emitting element into the waveguide, and escape from the element via a (part of a) face of the waveguide. As also indicated above, in embodiments the radiation exit window may optionally be configured as part of the external surface of the object. Another term for "escape" can be "outcoupling".

Especially, the (solid state) light source is at least controllable between a first UV radiation level and a second UV radiation level, wherein the first UV radiation level is larger than the second UV radiation level (and wherein the second UV radiation level is smaller than the first radiation level or may even be zero). Hence, in an embodiment the light source can be switched off and can be switched on (during a radiation stage). Further, optionally also the intensity of the UV radiation may be controlled between these two stages, such as a stepwise or continuous UV radiation intensity control. Hence, the light source is especially controllable (and thus its UV radiation intensity is).

In (aquatic (such as marine)) embodiments, the anti-biofouling system is especially configured to provide UV radiation to the part of the object or to water adjacent to this part. This especially implies that during an irradiation stage the UV radiation is applied. Hence, there may optionally also be periods wherein no UV radiation is applied at all. This may (thus) not only be due to e.g. a control system switching of one or more of the UV-emitting elements, but may e.g. also be due to predefined settings such as day and night or water temperature, etc. For instance, in an embodiment the UV radiation is applied in a pulsed way.

Hence, in a specific embodiment or aspect, the anti-biofouling system is configured for preventing or reducing biofouling on a fouling surface of an object that during use is at least temporarily exposed to water, by providing an anti-fouling light (i.e. UV radiation) to said fouling surface or water adjacent thereto. Especially, the anti-biofouling system may be configured to provide said anti-fouling light via an optical medium to said fouling surface, wherein the UV-emitting element further comprises (ii) said optical medium configured to receive at least part of the UV radiation (anti-fouling light), the optical medium comprising an emission surface configured to provide at least part of said UV radiation (anti-fouling light). Further, especially the optical medium comprises one or more of a waveguide and an optical fiber, and wherein the UV radiation (anti-fouling light) especially comprises one or more of UVB and UVC light. These waveguides and optical media are herein further not discussed in detail.

The optical medium may also be provided as a (silicone) foil for applying to the protected surface, the foil comprising at least one light source for generating anti-fouling light and a sheet-like optical medium for distributing the UV radiation across the foil. In embodiments the foil has a thickness in an order of magnitude of a couple of millimeters to a few centimeters, such as 0.1-5 cm, like 0.2-2 cm, or even smaller, such as in the range of 0.2-1 mm, like 0.4-1 mm. In embodiments, the foil is not substantially limited in any direction perpendicular to the thickness direction so as to provide substantially large foil having sizes in the order of magnitude of tens or hundreds of square meters. The foil may be substantially size-limited in two orthogonal directions perpendicular to the thickness direction of the foil, so as to provide an anti-fouling tile; in another embodiment the foil is substantially size-limited in only one direction perpendicular to a thickness direction of the foil, so as to provide an elongated strip of anti-fouling foil. Hence, the optical medium, and even also the UV-emitting element, may be provided as tile or as strip. The tile or strip may comprise a (silicone) foil.

Therefore, in specific embodiments the waveguide element may comprise one or more of glass, such as quartz glass, silicone and a light transmissive polymer. Hence, glass, silicone, or a light transmissive (organic) polymer may be applied as waveguide material.

In an embodiment the UV-emitting element comprises a two-dimensional grid of light sources for generating UV radiation and the optical medium is arranged to distribute at least part of the UV radiation from the two-dimensional grid of light sources across the optical medium so as to provide a two-dimensional distribution of UV radiation exiting the light emitting surface of the light module. The two-dimensional grid of light sources may be arranged in a chicken-wire structure, a close-packed structure, a rows/columns structure, or any other suitable regular or irregular structure. The physical distance between neighboring light sources in the grid may be fixed across the grid or may vary, for example as a function of light output power required to provide the anti-fouling effect or as function of the location of the UV-emitting element on the protected surface/surface to be kept clean (e.g. location on the hull of a ship). Advantages of providing a two-dimensional grid of light sources include that the UV radiation may be generated close to the areas to be protected with UV radiation illumination, and that it reduces losses in the optical medium or light guide and that it is increasing homogeneity of the light distribution. Preferably, the UV radiation is generally homogeneously distributed across the emission surface; this reduces or even prevents under-illuminated areas, where fouling may otherwise take place, while at the same time reducing or preventing energy waste by over-illumination of other areas with more light than needed for anti-fouling. In an embodiment, the grid is comprised in the optical medium. In yet another embodiment, the grid may be comprised by a (silicone) foil.

Further, in an embodiment the optical medium may be disposed proximate (including optionally attached to) the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

In a further aspect, the invention also provides a method of anti-(bio)fouling (a part of) an external surface of an object. For instance, lighting system light, especially UV radiation, may be provided as function of a sensor signal, a timer, and a user interface signal; see also above. Yet further, in an aspect the invention provides a method of controlling the system (as described herein), wherein the method comprises providing the lighting system light, especially UV radiation, may be provided as function of a sensor signal, a timer, and a user interface signal; see also above. As also indicated above, such sensor signal may e.g. be from a sensor configured to sense biofouling.

The light source may be configured external from such object and the radiation may be provided into the waveguide element e.g. via an optical fiber. In yet other embodiments, the light source is embedded in the waveguide element.

Herein, the term "object" may in specific embodiments also refer to an arrangement of (different) objects, which especially are functionally connected.

In yet a further aspect, the invention also provides a method of providing an (anti-biofouling) system to an object, the method comprising providing the (anti-biofouling) system (with in embodiments the waveguide element) to the object. Especially, the object may be configured to be at least temporarily exposed to harmful micro-organisms, such as bacteria, during use of the object. Hence, in embodiments the waveguide element may be attached to the object, to provide the objection comprising the waveguide element.

In embodiments, the invention also provides a method of providing an anti-biofouling system to an object, that during use is at least temporarily exposed to water, the method comprising providing, such as integrating in the object and/or attaching to an external surface, the anti-biofouling system to the object, such as a vessel, with the waveguide element configured to provide said UV radiation to one or more of a part of an external surface of the object and water (being) adjacent to said part (during use), as further defined in the accompanying claims. Especially, the waveguide element is attached to the external surface, or may even be configured as (first) part of the external surface.

The method of providing the system to an object may e.g. include applying at least part of the system, such as the UV emitting element, to an outer surface of the object. For instance, at least part of the system, such as the UV emitting element, may be attached to at least part of the outer surface of the object. This may be done with mechanical and/or adhesive fastening means.

In specific embodiments, the invention provides an embodiment of the method, wherein the method comprises providing a waveguide element arrangement as defined herein to an object, the method comprising providing the waveguide element arrangement to the object, wherein the object (already) comprises the waveguide element, and wherein the method further comprises applying the converter arrangement to the waveguide element, to provide the waveguide element arrangement to the object. Hence, an object already comprising a waveguide element arrangement may further be adapted by applying, such as by coating or printing, the converter arrangement to the waveguide element arrangement, such as by applying the converter arrangement to a radiation exit window from a waveguide element.

Hence, the invention may thus also provide a method comprising providing a sheet-like light output device as defined herein to an object, the method comprising providing the sheet-like light output device to the object, wherein the object (already) comprises the sheet-like light output device but without luminescent material, and wherein the method further comprises applying the luminescent material to the sheet-like light output device (without the luminescent material), to provide the sheet-like light output device (with the luminescent material) to the object.

Amongst others, the invention may be used to generate visible light for esthetic purpose (color, logo, etc.). The invention may also be used for continuously protecting the environment from exposure to excess UV level available that may otherwise occur in the surface areas directly above the positions above the LEDs if not shielded with luminescent material. In this way the overall UV output may in embodiments be adjusted by building luminescent material, in the panel design, to ensure that everywhere on the surface there is sufficient UV intensity for antifouling, while at the same time the exposure risk for external species (human, or larger sea life) is minimized. Hence, in embodiments excess UV radiation may be generated. This may allow using less (solid state) light sources. Excess UV, however, may at least partly be reduced by the presence of the luminescent material.

The visible and/or IR light may also be generated for monitoring the condition of the UV LEDs for the antifouling process. Hence, in specific embodiments there may also be a feedback, e.g. on the bases of a light sensor (for visible light), which may be used for controlling the intensity of the (solid state) light source(s) and/or for controlling its condition.

The terms "visible", "visible light" or "visible emission" refer to light having a wavelength in the range of about 380-780 nm.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 1a-1h schematically depict some general aspects.

The drawings are not necessarily to scale.

DETAILED DESCRIPTION OF THE EMBODIMENTS

Figure 1A:
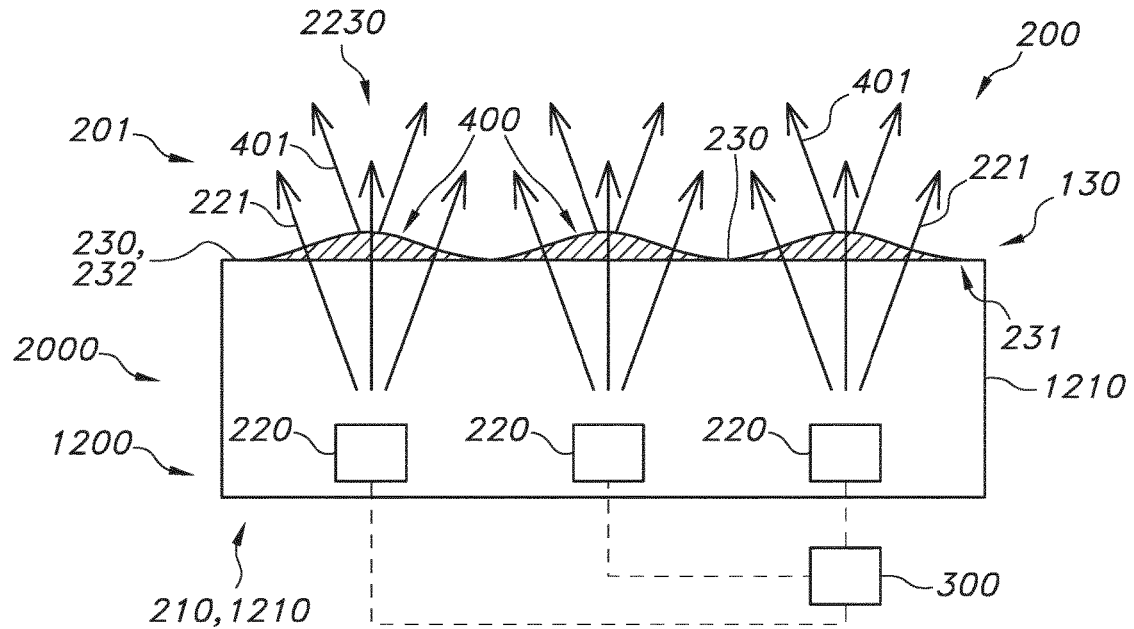

FIG. 1a schematically depicts an embodiment of an anti-biofouling system 200 which comprises an UV-emitting element 210. The UV-emitting element 210 comprises a UV radiation exit window 230. The UV-emitting element 210 at least partly encloses a light source 220 configured to provide UV radiation 221. Here, by way of example three light sources 220 are depicted. Here, the UV-emitting element 210 is configured as waveguide, with elements embedded therein. Hence, the light sources 220 are embedded in the waveguide. The UV radiation exit window 230 is configured to transmit at least part of the UV radiation 221 of the light source 220. The UV radiation exit window 230 comprises an upstream window side 231, here directed to the light source(s) and a downstream window side 232. Hence, FIG. 1a schematically depicts an embodiment of a system 200 comprising a light source 220 configured to generate light source radiation 221. The light source radiation 221 at least comprises UV radiation. The system 200 further comprises a luminescent material 400 configured to convert part of the light source radiation 221 into luminescent material radiation 401, wherein the luminescent material radiation 401 comprises visible light and/or IR radiation. As schematically shown, the system 200 is configured to generate system light 201 comprising the light source radiation 221 and the luminescent material radiation 401.

The system 200 is configured to generate system light 201 comprising the light source radiation 221 (including UV radiation) and the luminescent material radiation 401.

Here, by way of example the luminescent material 400 is inhomogeneously distributed over the radiation exit window 230. In this way, the intensity distribution of the light source radiation 221 may be spatially distributed relative homogeneously without substantial difference in intensity over the light emissive surface.

FIG. 1a, and many of the other drawings, may schematically depict a sheet-like light output device 2000 having a light emissive surface 2230. Such light emissive surface 2230 may have an area of e.g. at least 100 cm², such as in the range of 100-40,000 cm², though even larger may be possible. Further, the UV emitting element 210 or here sheet-like device 2000 may be provided as an array of such elements or device, by which a large surface area of an object may be covered (see also below).

Reference 300 refers to a control system for controlling the radiation 221 of the light sources 220, for instance as function of an optical sensor. Here, controlling may refer to one or more of controlling the intensity and controlling the spectral distribution.

Figure 1B:
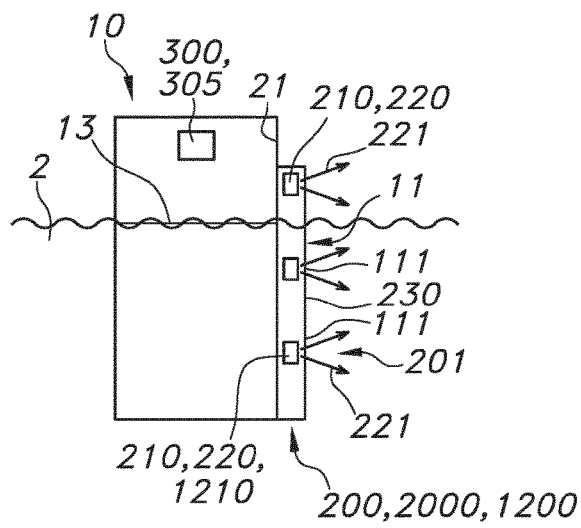
Figure 1C:
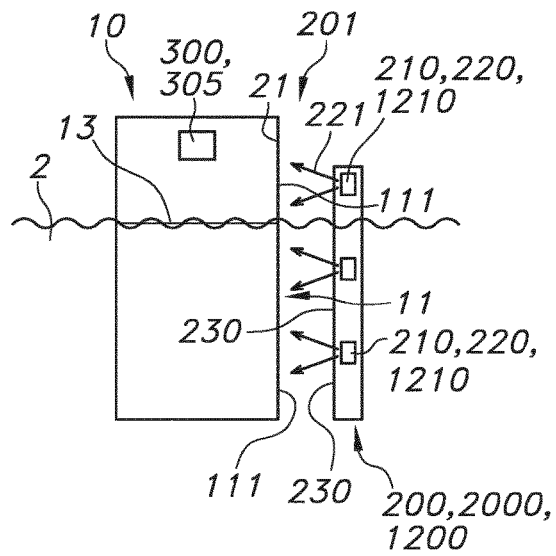

FIGS. 1b-1d schematically depict embodiments of an object 10 that during use is at least partly submerged in water 2, see the water line 13. The object 10, such as a vessel or a sluice, see also below, further comprises an anti-biofouling system 200 comprising an UV-emitting element 210, especially for application of UV radiation 221 to a part 111 of an external surface 11 of the object 10, such as a hull or part or a hull. Here, two embodiments are shown wherein the anti-biofouling system 200, or more especially the UV-emitting element 210 is part of an outer surface, and thereby forms in fact part of the outer surface (FIG. 1a) or wherein the UV-emitting element 210 is configured to irradiate the outer surface and does not necessarily form part of an outer surface, such as a hull of a ship (FIG. 1c). For instance, the object 10 is selected from the group consisting of a vessel 1 and an infrastructural object 15 (see also below).

The UV-emitting element 210 comprises one or more light sources 220 and may thus especially be configured to irradiate with said UV radiation 221 during an irradiation stage one or more of (i) said part 111 of said external surface 11 and (ii) water adjacent to said part 111 of said external surface 11. The former variant applies especially the embodiment of FIG. 1c, and the latter embodiment especially applies to both embodiments of FIGS. 1b-1c. Note however that when an external surface of the UV-emitting element 210 is configured as external surface of the object 10, of course the part 111 is irradiated per se with the UV radiation 21.

Hence, the UV-emitting element 210 comprises a UV radiation exit window 230 and the UV-emitting element 210 is configured to provide said UV radiation 221 downstream from said UV radiation exit window 230 of said UV-emitting element 210.

Especially, the light source 220 is at least controllable between a first UV radiation level and a second UV radiation level, wherein the first UV radiation level is larger than the second UV radiation level (and wherein the second UV radiation level is smaller than the first radiation level (including e.g. zero).

As indicated above, the term "vessel", indicated with reference 1, may e.g. refer to e.g. a boat or a ship (ref 10a in FIG. 1d), etc., such as a sail boat, a tanker, a cruise ship, a yacht, a ferry, a submarine (ref 10d in FIG. 1d), etc. etc., like schematically indicated in FIG. 1d. The term "infrastructural object", indicated with reference 15, may especially refer to aquatic applications that are in general arranged substantially stationary, such as a dam/sluice (references 10e/10f in FIG. 1d), a pontoon (ref. 10c in FIG. 1d), an oilrig (ref. 10b in FIG. 1d), etc. etc.

FIG. 1e schematically depicts in more detail an embodiment of the anti-biofouling system 200, here by way of example including an integrated control system 300 and an integrated sensor 310.

FIG. 1f schematically depicts an external surface 11 of an object 10, such as a vessel wall or a wall of an infrastructural object, with by way of example a plurality UV-emitting elements 210 (here associated to a hull 21 of a vessel 1). Alternatively or additionally, a plurality of functionally coupled or independently functioning anti-biofouling systems 200 may be applied.

FIG. 1f also schematically depicts the embodiment wherein the anti-biofouling system 200 comprises a plurality of UV-emitting elements 210 (with a plurality of light sources), a plurality of radiation exit windows 230, and a plurality of said parts 111, wherein the plurality of light sources 220 are configured to provide said UV radiation 221 via said plurality of radiation exit windows 230 to said plurality of parts 111, and wherein said plurality of parts 111 are configured at different heights of the object 10, and wherein the control system 300 is configured to control the light sources 220 individually as function of said input information. For instance, in an embodiment the control system 300 may be configured to control the light sources 220 individually as function of the positions of the parts 111 of the external surface 11 relative to the water.

Figure 1G:
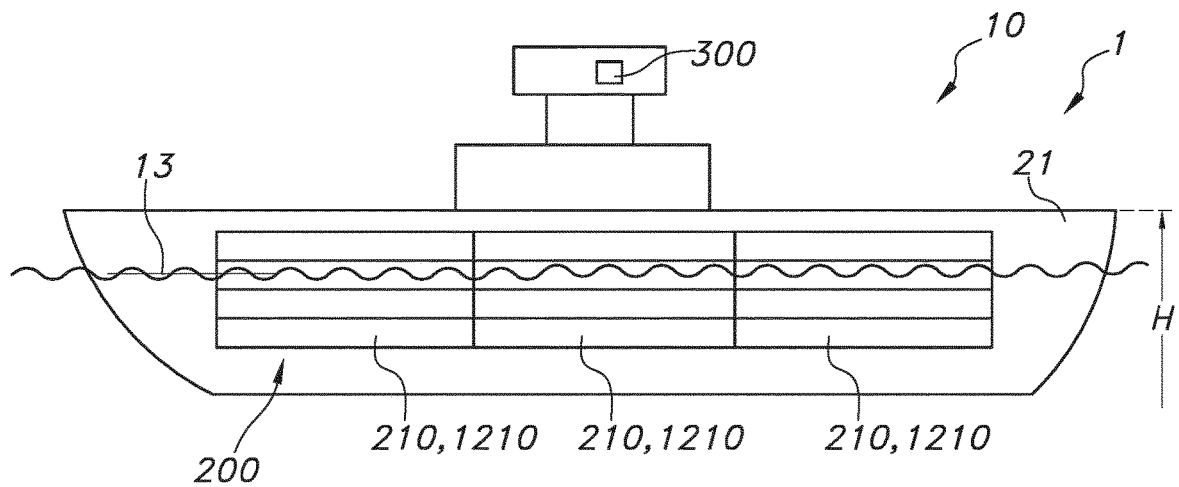

FIG. 1g schematically depicts an embodiment wherein a vessel 1, as embodiment of the object 10, comprises a plurality of anti-biofouling systems 200 and/or a one or more of such anti-biofouling systems 200 comprising a plurality of UV-emitting elements 210. Dependent upon the height of the specific such anti-biofouling system 200 and/or the height of the UV-emitting elements 210, such as relative to a water (line), the respective UV-emitting elements 210 may be switched on.

Figure 1H:
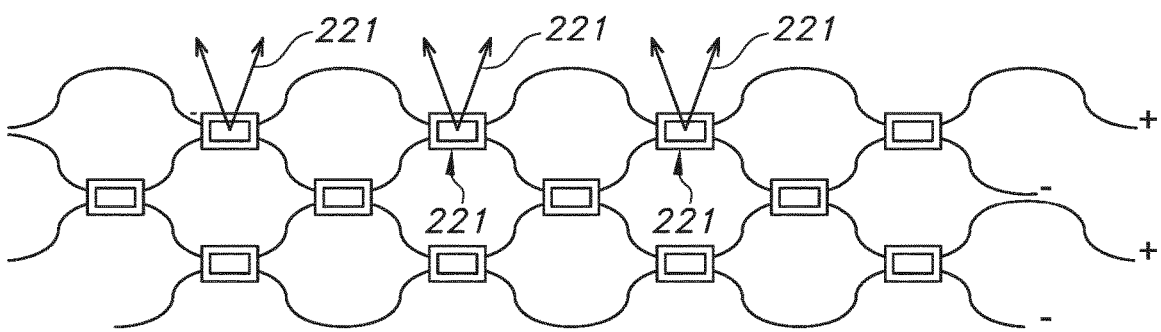

FIG. 1h shows a chicken-wire embodiment where light sources 210, such as UV LEDs, are arranged in a grid and connected in a series of parallel connections. The LEDs can be mounted at the nodes either through soldering, glueing or any other known electrical connection technique for connecting the LEDs to the chicken wires. One or more LEDs can be placed at each node. DC or AC driving can be implemented. If AC is used, then a couple of LEDs in anti-parallel configuration may be used. The person skilled in the art knows that at each node more than one couple of LEDs in anti-parallel configuration can be used. The actual size of the chicken-wire grid and the distance between UV LEDs in the grid can be adjusted by stretching the harmonica structure. The chicken-wire grid may be embedded in an optical medium. Above, especially active prevention applications are described, wherein the anti-biofouling system 200 switches off, or switches specific UV-emitting elements 210 or specific light sources 220 off, dependent upon contact with the water, a signal of a sensor, etc. etc. However, alternatively or additionally, also warning signals or messages may be used to warn a person of danger.

Figure 2A:
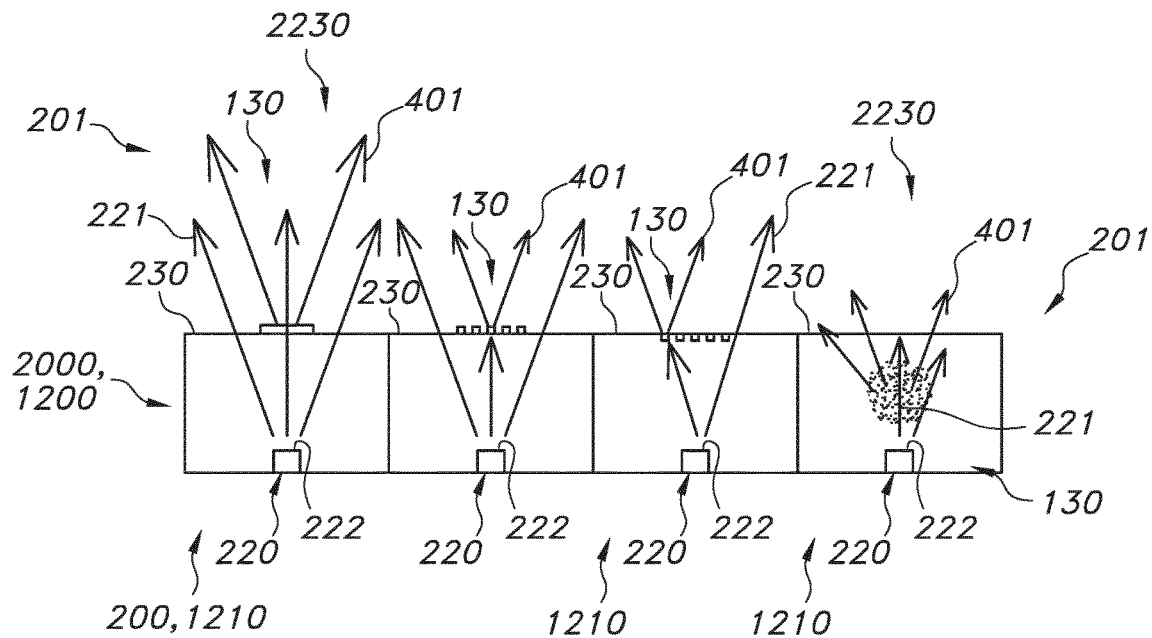
FIGS. 2a-2e schematically depict some embodiments and variants.

FIG. 2*a* schematically depicts four different embodiments of the system 200, actually shown as a single system 200 wherein different embodiments are depicted for illustration purposes. Four different possibilities, though more embodiments are possible, of a converter arrangement 130 are schematically depicted. From left to right; a closed layer covers part of a radiation exit window; the converter arrangement 130 comprises a pattern 131 of luminescent material 400 on the radiation exit window 230; the luminescent material 400 is embedded close to the radiation exit window 230; the luminescent material 400 is embedded in a waveguide element 1200.

Hence, FIG. 2*a* schematically depicts an embodiment of the system 200 comprising a waveguide element arrangement 1200, wherein the waveguide element arrangement 1200 comprises a waveguide element 1210 comprising a radiation exit window 230. Especially, the waveguide element 1210 is (a) configured to receive the light source radiation 221, and (b) configured to radiate (in an operation mode) part of the light source radiation 221 to the exterior of the waveguide element 1210 via the radiation exit window 230. Further, as indicated above the waveguide element arrangement 1200 further comprises a converter arrangement 130 comprising the luminescent material 400.

Figure 2B:
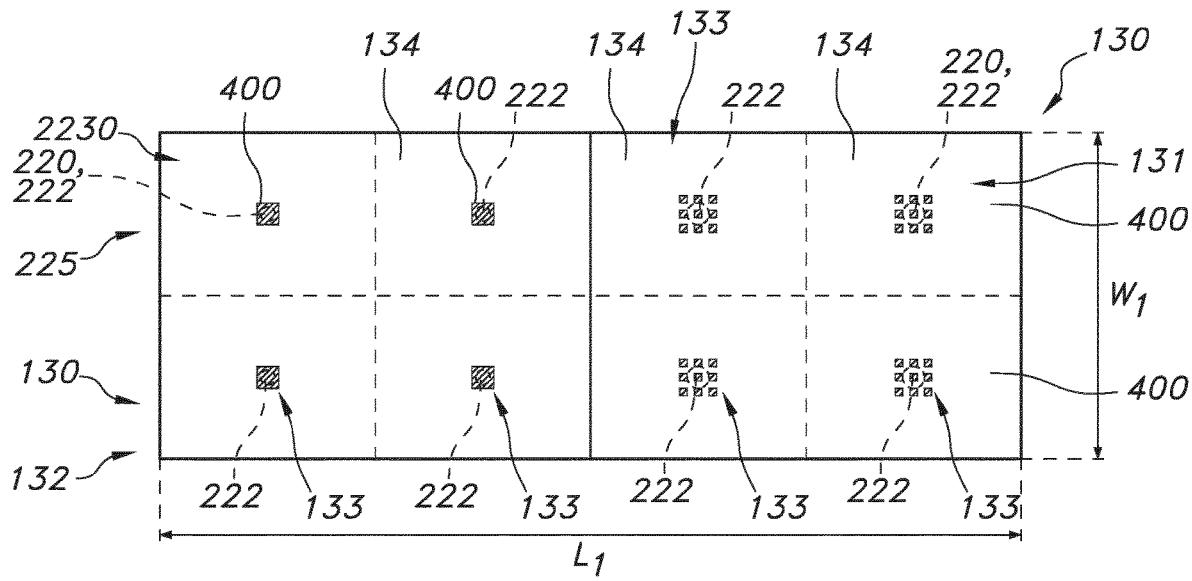

FIG. 2*b* schematically depicts an embodiment of the system 200, wherein the light source 220 (behind the plane of drawing) comprises a plurality of light emitting surfaces 222. Actually, FIG. 2*b* schematically depicts an embodiment with a plurality of light sources 220, each having a light emitting surface 222. Reference 131 indicates a pattern of luminescent material 400 (see also FIG. 2*a*).

The light sources 220 are configured to provide the light source radiation 221 via the plurality of light emitting surfaces 222. The light emitting surfaces are configured in a 2D light emitting surfaces array 225. Also the converter arrangement 130 comprises a 2D converter array 132 with a plurality of first areas 133 with the luminescent material 400 and one or more second areas 134 with no or less luminescent material 400. As shown, the 2D converter array 132 is aligned with the light emitting surfaces array 225. During operation of the system 200, the first areas 133 may receive more light source radiation 221 than adjacent second areas 134.

Figure 2C:
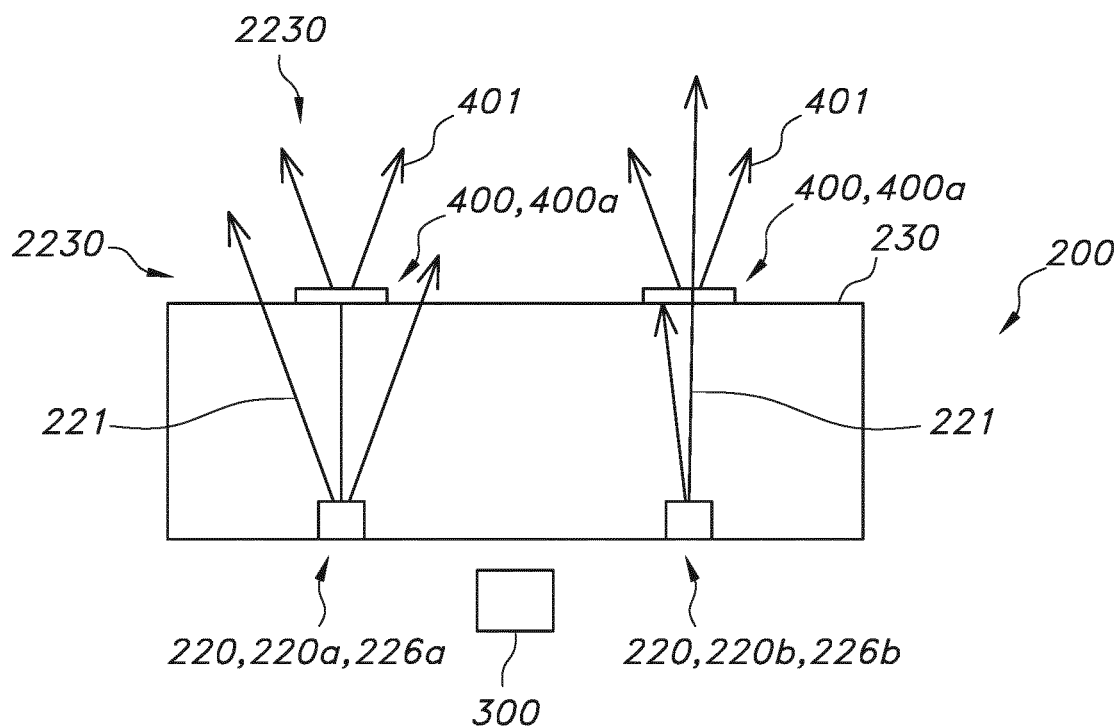

On the left in FIG. 2*b*, the system includes an area with closed patches of luminescent material 400, above each light source 220. However, one or more of (i) one or more of the plurality of the first areas 133 and (ii) one or more of the one or more second areas 134 are patterned. On the left, the system 200 includes an area wherein the first areas 133 are patterned. Here, the system 200 may include a light emissive surface 2230 having an area size of about a length L1 times a width FIG. 2*c* schematically depicts an embodiment of the system 200 comprising a plurality of light sources 220 of which two or more subsets 226*a*, 226*b*, . . . of light sources 220. These may be independently controllable, such as via control system 300. The system 200 further comprises a plurality of different luminescent materials 400*a*, 400*b*, . . . having different spectral distributions of the luminescent material radiation 401. Different combinations of subsets 226*a*, 226*b*, . . . of light sources 220 and luminescent materials 400*a*, 400*b*, . . . can be configured to provide the different spectral distributions of the luminescent material radiation 401. As indicated above, the system 200 may further comprises a control system 300 configured to control the plurality of light sources 220 for controlling one or more of the spectral distribution of the system light 201 and the spatial distribution of the system light 201. When switching on both light sources 220 as schematically depicted, the cross-sectional area of a beam of light source radiation 221 emanating from the light emissive surface 2230.

FIG. 2*c* also shows that the light emissive surface 2230 comprises the radiation exit window 230 and the luminescent material 400 (which does not cover the entire radiation exit window 230 of the waveguide element 2230).

Figure 2D:
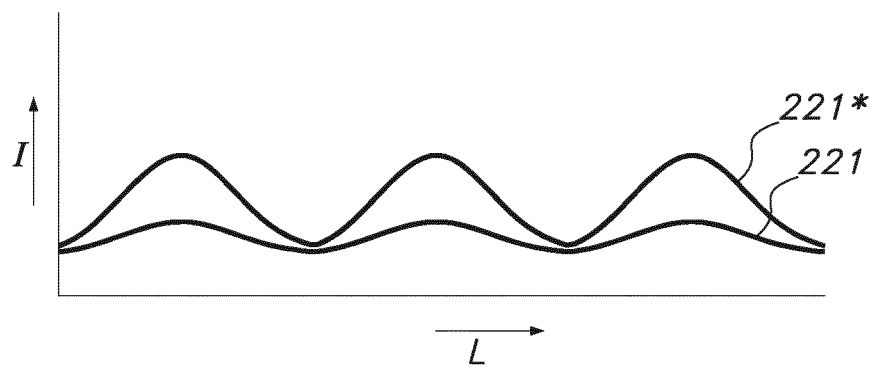

FIG. 2*d* very schematically depicts a spatial intensity distribution of the light source radiation 221, e.g. over a length L of a system, wherein three maxima are shown, e.g. due to the presence of three spatially separated light sources. The intensity of the radiation 221 is highest above such light sources and lowest between the light sources. The intensity distribution without the luminescent material 400 is indicated with 221*, and the intensity distribution with the availability of the luminescent material 400 as herein described is indicated with reference 221. Note that when desired also a general reduction of the intensity of the radiation 221 can be obtained, when e.g. even the minima of the radiation intensity without luminescent material 400 would be unnecessarily high.

Many schematical drawings herein schematically show embodiments wherein the light source 220 is embedded in the waveguide element 1210. The waveguide element comprises light transmissive material, through which the light source radiation may propagate.

Figure 2E:
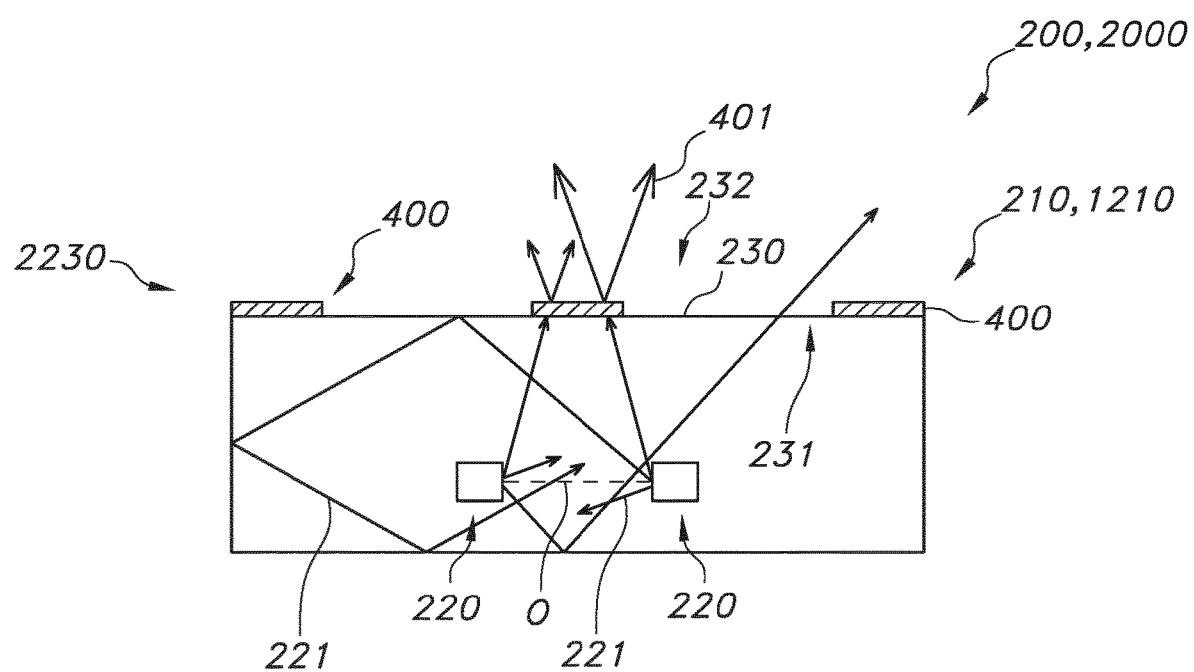

Many of the schematical drawings herein schematically show embodiments wherein the light sources provide light essentially directed to the radiation exit window. However, the one or more light sources may also be configured to provide the light source radiation substantially parallel to the radiation exit window, such as with the optical axis of the light source essentially parallel to the radiation exit window. FIG. 2*e* schematically depicts such embodiments, with by way of example only two light sources (but of course there can be many more). The optical axes, indicated with reference O, may essentially be parallel to the radiation exit surface 230. When a plurality of light sources is applied, the two or more of the optical axes may not be parallel (or antiparallel). In this way radiation may even be better distributed. Here, the light sources 220 are embedded in waveguide material. Light 221 of the light source(s) may be distributed over the waveguide element via total internal reflection (TIR), particularly at the bottom or top surface, as schematically depicted. Hence, the waveguide element is configured to waveguide the light source radiation. Part of the light source radiation 221 may also directly escape from the waveguide element, via the radiation exit window 230.

In the latter situation, the light source radiation propagates from the upstream side 231 to the downstream side 232 of the radiation exit window. On the radiation exit window 230, here (thus) on the downstream side 232, luminescent material 400 may be available. Hence, FIG. 2e schematically depicts embodiments wherein LED packages are used wherein a chip is mounted at 90 degrees angle to lead to the emission primarily taking place in the sideward direction (so along the waveguide (element)). The distribution process and the outcoupling of light from the waveguide material may be assisted by scattering in the waveguide and/or by scattering at the surface (e.g. by surface roughness). Outcoupling structures are known in the art. For instance, features having dimensions selected from the range of 0.1-10 µm may be applied, especially to create diffuse scattering. Alternatively or additionally, Fresnel lenses may be applied.

Figure 3A:
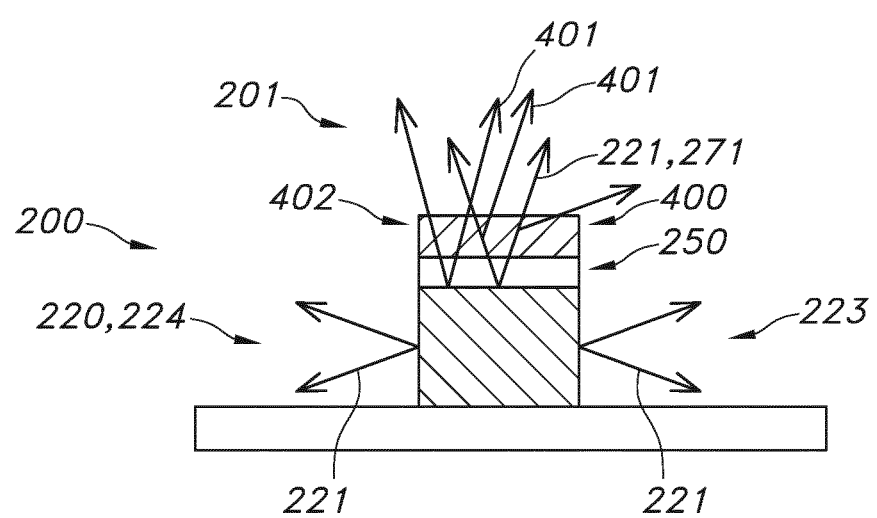
FIGS. 3a-3e schematically depict some further embodiments.

FIG. 3a schematically depicts an embodiment of a system 200 comprising a light source 220, a luminescent material 400 and a semi-transparent mirror 250. The light source 220 is configured to generate light source radiation 221, wherein the light source radiation 221 at least comprises UV radiation 271. The luminescent material 400 is configured to convert part of the light source radiation 221 into luminescent material radiation 401. The luminescent material radiation 401 comprises one or more of visible light and infrared radiation. The semi-transparent mirror 250 is configured downstream of the light source 220 and upstream of the luminescent material 400. Especially, the semi-transparent mirror 250 is configured to transmit part of the UV radiation 271 and to reflect at least part of the luminescent material radiation 401. As shown, the system 200 is configured to generate system light 201 comprising the light source radiation 221 and the luminescent material radiation 401.

As also shown in FIG. 3a, the light source 220, the semi-transparent mirror 250, and the luminescent material 400 are configured to provide at least part of the UV radiation 271 in a direction perpendicular to the semi-transparent mirror 250 and at least part of the UV radiation 271 in a direction parallel to the semi-transparent mirror 250. Hence, in fact the combination of light source 220 and semi-transparent mirror 250 provides a side emitter and top emitter.

Here, by way of example a solid state light source 224 is depicted, which includes a die 223. The die may be configured on a substrate, such as a PCB. The die may have a height of about 200-500 µm, but other thicknesses may also be possible. Hence, FIG. 3a also schematically displays such system 200 comprising the solid state light source 224, wherein the solid state light source 224 comprises a die 223.

As schematically depicted in FIG. 3a, the system 200 comprise in embodiments a package 260 comprising the solid state light source 224, the semi-transparent mirror 250, and the luminescent material 400. In the schematically depicted embodiment the semi-transparent mirror 250 is configured in optical contact with the die 223, and the luminescent material 400 is configured as luminescent material layer 402 on the semi-transparent mirror 250. In this embodiment, the semi-transparent mirror 250 is—by way of example—in physical contact with the die 223 and the luminescent material layer 402 is in physical contact with the semi-transparent mirror 250.

FIGS. 3b-3e schematically depict some variants wherein the system 200 includes a waveguide element 1210, such as a (thin) silicone layer. By way of example, two light sources 220 are depicted, but also a single light source 220 or a plurality of more than two of identical or different light sources 220 may be applied.

Figure 3B:
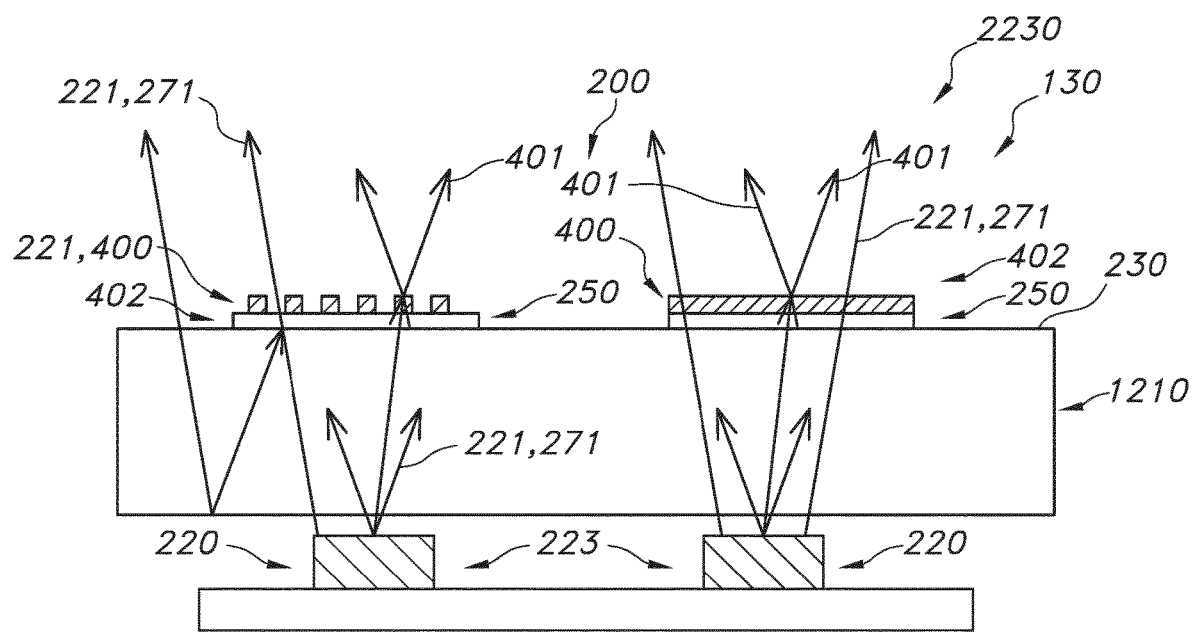
Figure 3C:
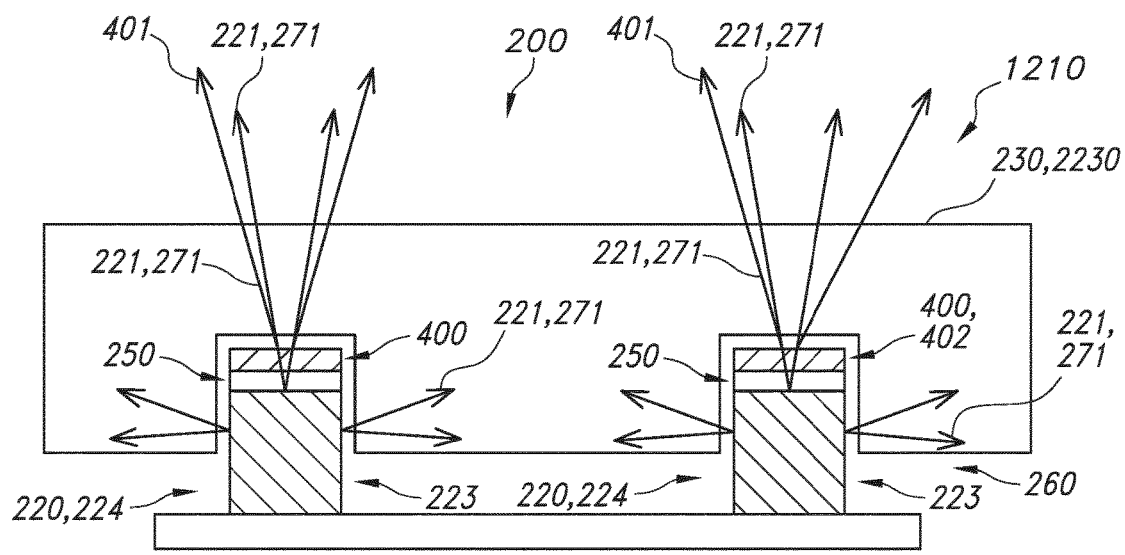
Figure 3D:
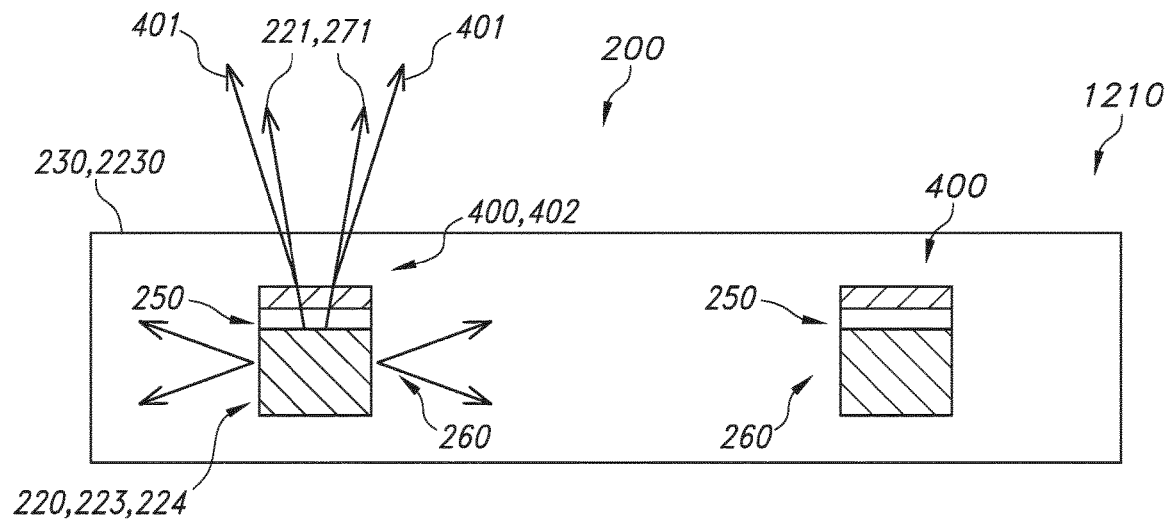
Figure 3E:
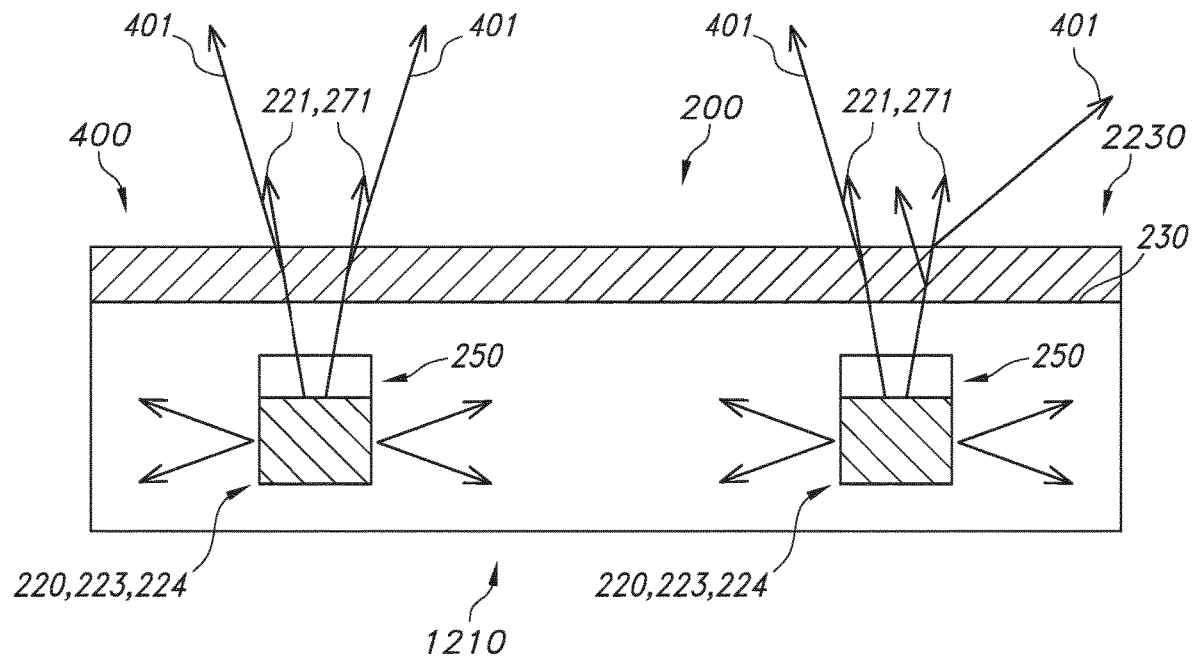

In FIG. 3b, the light source(s) 220 is (are) external from the waveguide element 1210. In FIG. 3c the light source(s) 220 is (are) partially embedded in the waveguide element 1210. In FIGS. 3d-3e, the light source(s) 220 is (are) (essentially) entirely embedded in the waveguide element 1210, such as a silicone layer or other layer of (organic) polymeric material.

In FIG. 3b the semi-transparent mirror 250 is configured downstream of the waveguide element 1210. The luminescent material 400 is configured downstream of the semi-transparent mirror 250, e.g. as (patterned) layer 402. The light sources 220 are configured upstream of the waveguide element 1210. The waveguide element 1210 includes an upstream face, and a downstream face, with here the latter having the semi-transparent mirror 250 configured on at least part of the downstream face. Note however, that the semi-transparent mirror 250 may also be provided on the entire downstream face in other embodiments (analogues to FIG. 3e, where, however, the luminescent material 400 is provided as layer 402 over the entire downstream face of the waveguide element 1210. Hence, e.g. the semi-transparent mirror 250 may be configured downstream of the waveguide element 1210 and upstream of the converter arrangement 130 comprising the luminescent material 400).

In FIG. 3c the entire package 260 is configured upstream of (at least part of) the waveguide element 1210. The configuration is chosen such, that at least part of the UV radiation 271 is provided in a direction perpendicular to the semi-transparent mirror 250, and escapes in this direction from the system, and at least part of the UV radiation 271 in a (second) direction parallel to the semi-transparent mirror 250 and enters the waveguide element 1210.

FIGS. 2a, 2c, 2e, and 3b schematically depict embodiments wherein the light emissive surface 2230 comprises the radiation exit window 230 and the luminescent material 400 (which does not cover (optionally in combination with a semi-transparent mirror 250) the entire radiation exit window 230 of the waveguide element 2230). As indicated above, the luminescent material 400 may in embodiments be configured on part of the radiation exit window 230. Luminescent material radiation 401 may escape from the luminescent material 400 and anti-biofouling light 271 may escape through the luminescent material 400 (when the layer of luminescent material 400 is (locally) thin enough and/are from the radiation exit window 230 where no luminescent material 400 is available. In such embodiments, the light emissive surface 2230 may comprise the layer of luminescent material 400 and the radiation exit window 230. FIGS. 3c and 3d, however, show embodiments wherein the light emissive surface 2230 is essentially identical with the radiation exit window 230; the radiation exit window 230 is especially a face of the waveguide element 1210.

FIG. 3d schematically depicts essentially the same embodiment as schematically depicted in FIG. 3c. However, now the light sources 220, more especially the entire packages 260, are embedded in the waveguide element 1210.

Hence, in embodiments the package(s) 260 may be configured at least partly embedded in the waveguide element 1210.

As shown in FIGS. 3c-3d, with solid state light sources with dies emitting in a plurality of directions, including emission from a top face of the die and emission from a side face of the die, both radiations may useful be used in the waveguide element.

FIG. 3e schematically depicts an embodiment wherein the luminescent material 400 is configured downstream of the waveguide element 1210. The light sources 220, however, and the accompanying semi-transparent mirrors 250, are embedded—though they may also be partly embedded—in the waveguide element 1210. Also in this way, at least part of the UV radiation 271 is provided in a direction perpendicular to the semi-transparent mirror 250, and may escape in this way from the system, as the mirror transmits part of the UV radiation, such as UV-C radiation. Further, at least part of the UV radiation 271 in a direction parallel to the semi-transparent mirror 250 and enters the waveguide element 1210. The UV radiation is distributed over the waveguide element 1210, and may escape elsewhere from the waveguide element 1210.

FIG. 3e schematically depicts an embodiment wherein the luminescent material 400 is available on the radiation exit window 230 of the waveguide element 1210. Hence, here the light emissive surface 2230 is essentially defined by the luminescent material 400.

Especially the embodiments of 3a, 3c, 3d and 3e may make use of the aspect that distribution of the UV radiation is done via radiation in a direction parallel to the semi-transparent mirror 250. For instance, in this way UV radiation 271 may be distributed over the waveguide element 1210, see FIGS. 3c, 3d and 3e. The above-mentioned first direction is a direction perpendicular to the semi-transparent mirror 250.

Referring to e.g. FIGS. 2a, 2b, 2c, 2e, 3b, 3c, 3d, and 3e, the system may be configured to radiate in an operation mode part of the light source radiation (to in specific embodiments the exterior of a sheet-like light output device) via the light emissive surface 2230 with an average power over time of at least $0.5\times10^{-9}$ Watt/mm$^2$, averaged over the light emissive surface 2230. Further, in embodiments—due to the configuration of the light sources, the luminescent material and the optional semi-transparent mirrors, the system may be configured to radiate in an operation mode part of the light source radiation 221 to the exterior of the waveguide element 1210 with a first average value of the power, averaged over the light emissive surface 2230, wherein the light source 220 and the converter arrangement 130 and the optional semi-transparent mirror(s) 250 (and optionally other optical elements) are configured such that a local maximum value of the power of the light source radiation 221 escaping from the light emissive surface 2230 is at maximum 15 times larger than the first average value of the power of the light source radiation 221.

Hence, in embodiments the invention provides an arrangement for generating anti-biofouling light. Such an arrangement is being proposed for controlling biofouling on e.g. the hull of a ship. The arrangement may comprise a light source for generating the anti-biofouling light and a light guide to communicate anti-biofouling light to areas where the light exits to light guide to control biofouling. The anti-biofouling light may be UVC light. To provide a sufficient intensity of anti-biofouling light at distances further away from the light source, the intensity of the anti-biofouling light nearer the light source usually is higher than needed to control biofouling closer to the light source. This surplus light may leave the light guide without being put to use or it may even result in a safety risk near a light source. It is an object of the invention disclosure to address the above drawbacks.

For instance, the invention may include an arrangement for generating anti-biofouling light, said arrangement comprising at least one light source for generating the anti-biofouling light, a light guide for receiving generated anti-biofouling light and communicating said anti-biofouling light to at least one area where anti-biofouling light escapes said light guide in order to control biofouling, wherein the arrangement further comprises a down-converting element for receiving generated anti-biofouling light and down-converting it to electromagnetic radiation of lower energy than the anti-biofouling light.

According to an embodiment the down-converting element comprises at least one phosphor-comprising substance.

According to an embodiment the light guide comprises a light guide layer comprising first and second surfaces that are parallel to the main direction in which anti-biofouling light is transported and the down-converting element is comprised on or near one of said first and second surfaces.

According to an embodiment the arrangement comprises a plurality of down-converting elements and said plurality is comprised in at least one of said first and second surfaces.

According to an embodiment the plurality of down-converting elements comprises different down-converting elements that down-convert anti-biofouling light to electromagnetic radiation having different energies levels, each energy level being lower than the energy level of the anti-biofouling light.

According to an embodiment the down-converting element is arranged to down-convert anti-biofouling light to visible light.

According to an embodiment the down-converting element is co-located with the light source, i.e. the light source and the down-converting element have the same in-plane position.

The invention further relates to an object comprising said arrangement said object being comprised in the group of objects comprising: a marine (fresh and sea water) object (e.g. vessel, oil rig, support structure for sea-based wind turbine, object for harvesting wave/tidal energy, pipe).

By down-converting anti-biofouling light to lower energies the safety risk of surplus anti-biofouling light, e.g. UVC light, escaping from the arrangement is reduced. By down-converting to visible light, surplus anti-biofouling light may be used to provide some kind of visual effect or to indicate the anti-biofouling arrangement has been turned on.

The term "plurality" refers to two or more.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A system comprising:
   a light source configured to generate light source radiation, wherein the light source radiation at least comprises UV radiation;
   a luminescent material configured to convert part of the light source radiation into luminescent material radiation, wherein the luminescent material radiation comprises one or more of visible light and infrared radiation, wherein the system is configured to generate system light comprising the light source radiation and the luminescent material radiation; and
   a semi-transparent mirror configured downstream of the light source and upstream of the luminescent material, wherein the semi-transparent mirror is configured to transmit part of the UV radiation and to reflect at least part of the luminescent material radiation.

2. The system according to claim 1, wherein the light source, the semi-transparent mirror, and the luminescent material are configured to provide at least part of the UV radiation in a direction perpendicular to the semi-transparent mirror and at least part of the UV radiation in a direction parallel to the semi-transparent mirror.

3. The system according to claim 1, comprising a solid state light source, wherein the solid state light source comprises a die, wherein the system comprises a package comprising the solid state light source.

4. The system according to claim 3, wherein the package further comprises the semi-transparent mirror.

5. The system according to claim 4, wherein the package further comprises the luminescent material.

6. The system according to claim 5, wherein the semi-transparent mirror is configured to be in physical contact with the die, and wherein the luminescent material is configured as luminescent material layer on the semi-transparent mirror.

7. The system according to claim 6, comprising:
   a plurality of the light sources, wherein each light source is configured to generate light source radiation, wherein the light source radiation at least comprises UV radiation,
   the luminescent material configured to convert part of the light source radiation of each of the light sources into the luminescent material radiation, wherein system light comprises the light source radiation of each of the light sources and the luminescent material radiation.

8. The system according to claim 7, further comprising a plurality of the semi-transparent mirrors, configured downstream of each of the light sources and upstream of the luminescent material.

9. The system according to claim 8, wherein each of the light source and each of the semi-transparent mirror are configured to provide at least part of the UV radiation of the respective light source in a direction perpendicular to the respective semi-transparent mirror and at least part of the UV radiation of the respective light source in a direction parallel to the respective semi-transparent mirror.

10. The system according to claim 7, wherein all light sources comprise solid state light sources.

11. The system according to claim 1, wherein the system is configured to radiate in an operation mode part of the light source radiation to the exterior of a light output device via a light emissive surface with an average power over time of at least $0.5 \times 10^{-9}$ Watt/mm$^2$, averaged over the light emissive surface, and wherein the light source radiation comprises UV-C radiation.

12. The system according to claim 1, comprising a waveguide element arrangement, wherein the waveguide element arrangement comprises a waveguide element comprising a radiation exit window, wherein the waveguide element is configured to receive the light source radiation, and configured to radiate in an operation mode part of the light source radiation to the exterior of the waveguide element via the radiation exit window.

13. The system according to claim 12, wherein the waveguide element arrangement further comprises a converter arrangement comprising the luminescent material.

14. The system according to claim 13, wherein a semi-transparent mirror is configured downstream of the waveguide element and upstream of the converter arrangement.

15. The system according to claim 12, wherein the light source is at least partly embedded in the waveguide element.

16. The system according to claim 5, comprising a plurality of the packages, each package configured at least partly embedded in a waveguide element.

17. The system according to claim 13, wherein the system comprises a light emissive surface wherein the system is configured to radiate in an operation mode part of the light source radiation to the exterior of the waveguide element with a first average value of the power, averaged over the light emissive surface, wherein the light source and the converter arrangement are configured such that a local maximum value of the power of the light source radiation escaping from the light emissive surface is at maximum 15 times larger than the first average value of the power of the light source radiation.

18. The system according to claim 13, wherein the converter arrangement comprises a pattern of luminescent material on the radiation exit window wherein the light source is at least partly embedded in the waveguide element, and wherein the pattern of luminescent material is configured to reduce intensity differences of light source radiation over the light emissive surface.

19. The system according to claim 12, wherein the waveguide element is watertight.

20. The system according to claim 12, wherein the system is an anti-biofouling system.

* * * * *